US012702424B2

(12) United States Patent
Trivisani

(10) Patent No.: US 12,702,424 B2
(45) Date of Patent: Aug. 11, 2026

(54) UMBILICAL CORD CLAMP AND WIRELESS TAG SYSTEMS, METHODS, AND APPARATUS

(71) Applicant: Divergent Medical Technologies, LLC, Oakland, NJ (US)

(72) Inventor: Dean Trivisani, Oakland, NJ (US)

(73) Assignee: Divergent Medical Technologies, LLC

( * ) Notice: Subject to any disclaimer, the term of this patent is extended or adjusted under 35 U.S.C. 154(b) by 74 days.

(21) Appl. No.: 18/806,873

(22) Filed: Aug. 16, 2024

(65) Prior Publication Data

US 2024/0398422 A1 Dec. 5, 2024

Related U.S. Application Data

(63) Continuation-in-part of application No. 17/848,576, filed on Jun. 24, 2022, now Pat. No. 12,064,299.

(51) Int. Cl.
*A61B 17/122* (2006.01)
*A61B 90/90* (2016.01)

(52) U.S. Cl.
CPC ............ *A61B 17/122* (2013.01); *A61B 90/90* (2016.02)

(58) Field of Classification Search
CPC .................. A61B 17/122; A61B 90/90; A61B 2017/00084; A61B 2017/00119; A61B 2017/00203; A61B 2017/00221; A61B 2017/0023; A61B 2017/00734; A61B 2017/00902; A61B 2034/2048; A61B 2090/0814; A61B 90/98; G16H 10/60; G16H 10/65; G16H 40/67
See application file for complete search history.

(56) References Cited

U.S. PATENT DOCUMENTS

| | | | | |
|---|---|---|---|---|
| 5,440,295 | A | 8/1995 | Ciecwisz et al. | |
| 5,902,933 | A * | 5/1999 | Bingo | G01L 9/0072 361/283.4 |
| 7,106,191 | B1 | 9/2006 | Liberati | |
| 2002/0101353 | A1 | 8/2002 | Radomsky et al. | |

(Continued)

FOREIGN PATENT DOCUMENTS

| | | | |
|---|---|---|---|
| GB | 2102998 | A | 2/1983 |
| GB | 2407935 | A | 5/2005 |
| GB | 2420289 | A | 5/2006 |

*Primary Examiner* — Omeed Alizada
(74) *Attorney, Agent, or Firm* — Gearhart Law LLC

(57) ABSTRACT

Systems, methods, and apparatus are disclosed involving an electronic medical records (EMR) system and security platform adapted for the safety and security of newborn babies. An exemplary device comprises a wireless-enabled umbilical cord clamp apparatus having a wireless-enabled tag and a tamper-evident switch. An exemplary system further includes a server, a wireless transceiver, a console apparatus, and a wireless-enabled umbilical cord clamp apparatus. The wireless transceiver may act as a tag reader within a matrix of other tag readers distributed throughout a hospital. The console interacts with the wireless tag and the server. The wireless tag is used to generate location data and status data for determination by the server and/or console of the location and status of the clamp apparatus within the hospital matrix. The server and/or console may receive and interpret such tag data, and compute appropriate responses thereof, such as locking down hospital perimeter doors.

7 Claims, 17 Drawing Sheets

(56) References Cited

U.S. PATENT DOCUMENTS

| | | | | |
|---|---|---|---|---|
| 2004/0199178 | A1 | 10/2004 | Small | |
| 2010/0211080 | A1* | 8/2010 | Trivisani | A61B 90/98 606/120 |
| 2013/0182382 | A1 | 7/2013 | Vardi et al. | |
| 2023/0070528 | A1* | 3/2023 | Muramoto | G01K 1/14 |

* cited by examiner

System Functions 80000
System 80010
Server 81010
Server Functions 81000
Server Output APU Input Function 80100
APU Output Server Input Function 80400
Auxiliary Processing Unit 82010
APU Functions 82000
APU Output Tag or Console Input Function 80200
Tag or Console Output APU Input Function 80300
Tag or Console 83010
Tag or Console Functions 83000

Wireless Tags 100000

UMBILICAL CORD CLAMP AND WIRELESS TAG SYSTEMS, METHODS, AND APPARATUS

CROSS REFERENCE TO RELATED APPLICATION

This application claims priority to U.S. application Ser. No. 17/848,576 filed on Jun. 24, 2022, the contents of which is herein fully incorporated by reference in its entirety.

FIELD OF THE EMBODIMENTS

The embodiments of the present invention relate to systems, methods, and apparatus involving umbilical cord clamps, networked platforms for tracking umbilical cord clamps within a hospital, and in a particular embodiment, to an umbilical cord clamp tag and a system (to secure and protect newborn infants) involving at least one umbilical cord clamp and/or clamp tag adapted to be tracked wirelessly, at least one console unit adapted to wirelessly track the umbilical cord clamp, a server in communication (either via wired or wireless means) with the console unit that communicates clamp status content to the console unit, and at least one wireless transceiver adapted to wirelessly communicate with the umbilical cord clamp and/or clamp tag, the console, and/or the server, wherein the clamp status content is determined based in part on the position, location, operation, and integrity of the clamp, and the clamp's location relative to console unit, wireless transceiver, or server. In particular, the clamp integrity status reflects whether the clamp is intact and engaged, versus damaged and/or disengaged, indicating the possibility that an unauthorized person has tampered with the clamp and/or clamp tag.

BACKGROUND OF THE EMBODIMENTS

The related art includes, for instance, tools, products, and systems, including simple umbilical cord clamps to clamp umbilical cords of newborns to prevent bleeding at the umbilical cord; including umbilical cord tags, wrist tags, and ankle tags to identify the newborn and/or to indicate information about the newborn, such as the newborn's date of birth or blood type; and including tracking tags adapted to be attached to an umbilical cord clamp, a wrist, or an ankle, to track newborns, such as using bar codes printed on the tag, or a radio-frequency identification (RFID) transmitter in the tag. Inasmuch as tracking tags and umbilical cord clamps historically have served distinct, unrelated functions, conventional prior art technologies have separated tracking tags and umbilical cord clamps as distinct, unrelated devices, systems, and data collection sources. Conventional tracking tags have had limited tamper-indication capabilities, and such tamper-indication capabilities have included the capability to detect if a wrist band or ankle band has been cut, and the capability to detect if a wrist band, an ankle band, or an umbilical cord tag ceases to be in contact with the skin of a wearer.

In a conventional hospital setting according to the prior art, immediately after a newborn baby is born, hospital staff clamp an umbilical cord of the newborn baby, to stop blood from flowing within the umbilical cord, and then cut the umbilical cord of the newborn baby, with the clamp between the cut and the newborn to stop the umbilical cord from bleeding out from the newborn. Shortly after the newborn is born, the hospital staff prepare a tag identifying the newborn and attach the tag to the newborn around the newborn's umbilical cord clamp, wrist band, or ankle band in a fashion that prevents the tag from being removed without cutting the tag. In modern hospitals, the tag may include a radio-frequency identification (RFID) transmitter or a bar code that allows hospital staff to track, record, and document interactions with the newborn as a patient of the hospital, such as for monitoring, moving, feeding, treating, securing, and caring for the newborn. In particular, many hospitals have and use sophisticated security procedures, such as multiple checks of identification of visitors and employees, and security systems, such as double-locked doors and entrances ("mantraps"), to secure maternity wards and newborn wards, to prevent threat or abduction of babies.

In contrast to the prior art, the present invention and its embodiments are unique in its design, in its functionality, and in its intended use of the present invention. The present invention is unlike prior art concepts that have approached umbilical cord clamp technology and newborn tracking technology from other angles. The prior art lacks a dedicated platform that serves and manages clamp integrity, tamper monitoring, and location tracking in a wireless network within a wirelessly-networked environment. In contrast, the present solution seeks to pioneer the seamless wireless tracking of clamp tamper-evident integrity and location in newborns wearing wireless-enabled clamps within hospitals.

As described below, embodiments of the present invention include the use of novel features within a wireless-enabled platform comprising a tracking system involving multiple system components including at least one wireless transceiver, at least one server, at least one console unit, and at least one wireless-enabled umbilical cord clamp and/or clamp tag, the system and system components running software adapted to track, record, notify and/or alert users, and document status content data relative to a newborn, using systems and methods different from those of the prior art systems and methods.

BRIEF SUMMARY OF THE EMBODIMENTS

The embodiments of the present invention relate to systems, methods, and apparatus involving components that may be combined in multiple ways and may include one or more of a wireless-enabled umbilical cord clamp tag, a wireless transceiver, a wireless-enabled console unit, and/or a server, adapted to operate within a wirelessly-networked environment, such as a hospital, for treatment, identification, and tracking of newborns.

In a hospital setting according to the present invention, immediately after a newborn baby is born, hospital staff use an umbilical cord clamp to clamp an umbilical cord of the newborn baby, to stop blood from flowing within the umbilical cord, and then cut the umbilical cord of the newborn baby, with the clamp between the cut and the newborn to stop the umbilical cord from bleeding out from the newborn. The wireless-enabled umbilical cord clamp tag includes a processor, sensors, a power supply, and wireless communication circuitry to enable wireless programming and communication to and from the clamp and/or clamp tag, so that shortly after the newborn is born, the hospital staff may program the clamp and/or clamp tag to identify the newborn and to monitor the newborn within the hospital. The clamp tag is secured to the newborn's umbilical cord with an umbilical cord clamp in a fashion that prevents the umbilical cord clamp and/or clamp tag from being removed without triggering an alert or an alarm within the monitoring system.

Some embodiments of the present invention may use a wireless-enabled tag according to aspects of the present invention, in which the wireless-enabled tag is integrated with and in a novel umbilical cord clamp as a single assembly, in which the novel umbilical cord clamp may clamp an umbilical cord in a fashion similar to that of a conventional umbilical cord clamp. Some other embodiments of the present invention may use a wireless-enabled clamp tag according to aspects of the present invention, in which the wireless-enabled tag is adapted for use with a conventional umbilical cord clamp, such as being placed in the conventional annular hinge portion of the clamp, which activates a switch or button in the tag when the clamp is closed and the hinge portion presses against and depresses the switch or button. In some embodiments, the switch or button is raised relative to a cylindrical column inserted into the annual hinge portion. In other embodiments, the switch or button may be recessed in a cavity of the cylindrical column or other portion of the tag. In other embodiments, the switch or button may comprise a pressure-sensitive thin-film switch strip that is adapted to be inserted along and between an upper row of teeth and a lower row of teeth of the clamp, in which closure of the clamp involves the upper row of teeth engaging the switch strip and the umbilical cord in pressing them against the lower row of teeth of the clamp. In yet other embodiments, other sensing technologies may be employed to achieve the same end means as with the described buttons and switches.

In accordance with a first aspect of the invention, a wireless-enabled umbilical cord clamp apparatus is disclosed that is adapted for use in monitoring location of and detecting tampering with the wireless-enabled umbilical cord clamp apparatus, in which the clamp apparatus comprises: tag apparatus electronic circuitry and hardware including: a tag apparatus processor; a tag apparatus memory, the tag apparatus memory coupled to the tag apparatus processor; a tag apparatus wireless data transfer module, the tag apparatus data transfer module coupled to the tag apparatus processor; a tag apparatus wireless data transfer device, the tag apparatus data transfer device coupled to the tag apparatus processor; and a tag tamper-evident switch, the tag tamper-evident switch coupled to the tag apparatus processor; tag apparatus electronic software, the apparatus software stored in the apparatus electronic circuitry and hardware and adapted to enable, drive, and control the apparatus electronic circuitry and hardware; a tag apparatus power supply, the apparatus power supply coupled to and adapted to power the apparatus electronic circuitry and hardware; and a tag apparatus housing, the tag apparatus housing comprising a tag apparatus exterior and a tag apparatus interior, the tag apparatus interior containing the tag apparatus software, the tag apparatus power supply, and at least some of the tag apparatus electronic circuitry and hardware; wherein the tag apparatus exterior comprises a clamp apparatus frame adapted to be secured adjacent an umbilical cord of a newborn baby when the umbilical cord is clamped by an umbilical cord clamp; wherein the apparatus electronic circuitry and hardware are adapted to operate as a wireless tag that is adapted to be wirelessly read by a wireless tag reader comprising a wireless transceiver; wherein the wireless tag reader is adapted to be communicate to a server managing location data and status data applicable to the wireless tag; and wherein the tag tamper-evident switch is secured by the tag apparatus housing, is exposed in part to the tag apparatus exterior, is coupled to the tag apparatus electronic circuitry within the interior, and is adapted to be activated, deactivated, triggered, or tripped by efforts to tamper with the wireless tag or the umbilical cord clamp. The wireless tag also may be adapted to be read by and/or communicate with a console assembly or apparatus, such as for use by a nurse in a hospital maternity ward.

With respect to an exemplary server in communication with the apparatus of a first aspect of the invention, an exemplary server comprises: server electronic circuitry and hardware including: a server processor; a server memory, the server memory coupled to the server processor; a server data transfer module, the server data transfer module coupled to the server processor; a server data transfer device, the server data transfer device coupled to the server processor; server electronic software, the server software stored in the server electronic circuitry and hardware and adapted to enable, drive, and control the server electronic circuitry and hardware; a server power supply connection, the server power supply connection coupled to the electronic circuitry and hardware and couplable to a server power supply.

With respect to an console assembly adapted to read or communicate with the clamp apparatus of first aspect of the invention, an exemplary console assembly may include: console electronic circuitry and hardware including: a console processor; a console camera, the console camera coupled to the console processor; a console display, the console display coupled to the console processor; a console memory, the console memory coupled to the console processor; a console positioning device, the console positioning device coupled to the console processor; a console data transfer module, the console data transfer module coupled to the console processor; a console data transfer device, the console data transfer device coupled to the console processor; console electronic software, the console software stored in the console electronic circuitry and hardware and adapted to enable, drive, and control the console electronic circuitry and hardware; a console power supply connection, the console power supply connection coupled to the console electronic circuitry and hardware and couplable to a console power supply; and a console housing, the console housing comprising a console interior and a console exterior, the console interior containing the console electronic circuitry and hardware, the console software, and the console power supply connection; and the console exterior comprising a console frame enclosing the console interior.

In some embodiments, the data transfer device may be adapted to enable a wired or wireless data transfer between the console and a separate computing device, wherein the data transfer device may be adapted to enable the console to communicate with and transfer the electronic data feed to the separate computing device and to enable the separate computing device to communicate with and transfer electronic data to the console. The data transfer device may include, for example, a wire cable, a wireless transceiver, or both. The console may be enabled to transfer to, and/or receive from, the separate computing device data, software, and a configuration file, and the separate computing device may be enabled to transfer to the console other software and files. The wire cable, or a separate power cable, also may be adapted to power the console and/or enable the console to recharge the internal power source when the cable is coupled to an external power source.

In accordance with a second aspect of the invention, a system is disclosed that is adapted for use in monitoring location and status of, managing status and events of, and detecting tampering with a wireless-enabled umbilical cord clamp apparatus, the system comprising: a server comprising: server electronic circuitry and hardware including: a server processor; a server memory, the server memory coupled to the server processor; a server data transfer module, the server data transfer module coupled to the server processor; a server data transfer device, the server data transfer device coupled to the server processor; server electronic software, the server software stored in the server electronic circuitry and hardware and adapted to enable, drive, and control the server electronic circuitry and hardware; and a server power supply connection, the server power supply connection coupled to the server electronic circuitry and hardware and couplable to a server power supply; wherein the server is adapted to determine location data and status data, interpret determinations of location data and status data, determine responses to interpretations of location data and status data, and communicate responses, based on receiving location data and status data from within the system; a wireless transceiver in communication with the server data transfer device and the server data transfer module; a wireless-enabled umbilical cord clamp apparatus comprising: tag apparatus electronic circuitry and hardware including: a tag apparatus processor; a tag apparatus memory, the tag apparatus memory coupled to the tag apparatus processor; a tag apparatus wireless data transfer module, the tag apparatus data transfer module coupled to the tag apparatus processor; a tag apparatus wireless data transfer device, the tag apparatus data transfer device coupled to the tag apparatus processor; and a tag tamper-evident switch, the tag tamper-evident switch coupled to the tag apparatus processor; tag apparatus electronic software, the apparatus software stored in the apparatus electronic circuitry and hardware and adapted to enable, drive, and control the apparatus electronic circuitry and hardware; a tag apparatus power supply, the apparatus power supply coupled to and adapted to power the apparatus electronic circuitry and hardware; and a tag apparatus housing, the tag apparatus housing comprising a tag apparatus exterior and a tag apparatus interior, the tag apparatus interior containing the tag apparatus software, the tag apparatus power supply, and at least some of the tag apparatus electronic circuitry and hardware; wherein the tag apparatus exterior comprises a clamp apparatus frame adapted to be secured adjacent an umbilical cord of a newborn baby when the umbilical cord is clamped by an umbilical cord clamp; wherein the apparatus electronic circuitry and hardware are adapted to operate as a wireless tag that is adapted to be wirelessly read by a wireless tag reader comprising the wireless transceiver; wherein the wireless tag reader is adapted to be communicate to the server managing location data and status data applicable to the wireless tag; and wherein the tag tamper-evident switch is secured by the tag apparatus housing, is exposed in part to the tag apparatus exterior, is coupled to the tag apparatus electronic circuitry within the interior, and is adapted to be activated, deactivated, triggered, or tripped by efforts to tamper with the wireless tag or the umbilical cord clamp.

In an exemplary embodiment of the system, each console or clamp apparatus unit may include at least one configuration of the plurality of configurations. A configuration may include, for instance, a map (e.g., a floorplan of a hospital, an aerial map of the hospital, a road map of roads surrounding a hospital, a topography map of land surrounding a hospital, a resources map of resources within a hospital, a route map of a tag being relocated, a perspective view map, a plan view map, a point-of-view map, etc.), a user interface ("UI") utility (e.g., switch points of view, reveal details, switch profiles, synchronization of accounts, etc.), a terrain (e.g., a hospital, a parking lot, a city, a town, etc.), a tool (e.g., a clamp cutter, a vehicle, a unit or type of medication, a unit or type of nutrition, etc.), a capability (e.g., applying, attaching, cutting, removing, etc.), an avatar (e.g., a nurse, a doctor, a patient, a newborn baby, an expectant mother, a post-delivery mother, a father, etc.), and a communication utility (e.g., an electronic medical records (EMR) interface, a social media connection, a message feed, etc.). A user of the platform may include, for instance, a nurse, a doctor, a patient, a consumer, a producer, a performer, a business, a developer, an administrator, etc., or a combination thereof. A user may create and/or distribute a configuration, or both, by using the platform for user-based creation and/or distribution of configurations. Each configuration may be software code in a configuration file that includes, for instance, one or more of a settings file, a configuration file, a profile file, an applet file, an application file, a plug-in file, an application programming interface ("API") file, an executable file, a library file, an image file, a video file, a text file, a database file, a metadata file, and a message file. A producer user may develop the software code for the configuration file using, for instance, programming in coding languages, such as JavaScript and HTML, including open-source code, or object-oriented code assembly. The software code would be adapted to be compatible with and executable by the software of a console (e.g., an iPhone smartphone, smart watch, laptop computer, tablet, or the like or some combination thereof) on which a compatible video may be displayed, with which or within which the configuration would be used.

In an exemplary embodiment, the system may include the apparatus of the first aspect of the invention, in which the apparatus is adapted and configured to interact with the platform. The system further may be adapted to enable, permit, and allow a plurality of users to interact with each other, against each other, with one or more system-generated team members, or a combination thereof. The system may be adapted to enable, permit, and allow a user to associate content with a location, a topic, and/or a subject matter, and to push such associated content to another user who is at said location, who is interested in said topic, and/or who is connected to said subject matter.

In accordance with a third aspect of the invention, a method for is disclosed that is adapted for use in monitoring location of and detecting tampering with a wireless-enabled umbilical cord clamp apparatus, in which the method comprises: providing an apparatus, the apparatus adapted to be coupled to and in communication with a server; generating location data and status data of and by the apparatus; transmitting the location data and status data from the apparatus to the server; receiving the location data and status data from the apparatus at the server; determining the location data and the status data by the server; interpreting the location data and status data based on the determinations by the server; determining responses to the interpretations made by the server; and communicating the responses to a response recipient based on interpretations; wherein the wireless-enabled umbilical cord clamp apparatus comprises: tag apparatus electronic circuitry and hardware including: a tag apparatus processor; a tag apparatus memory, the tag apparatus memory coupled to the tag apparatus processor; a tag apparatus wireless data transfer module, the tag apparatus data transfer module coupled to the tag apparatus processor; a tag apparatus wireless data transfer device, the tag apparatus data transfer device coupled to the tag apparatus processor; and a tag tamper-evident switch, the tag tamper-evident switch coupled to the tag apparatus processor; tag apparatus electronic software, the apparatus software stored in the apparatus electronic circuitry and hardware and adapted to enable, drive, and control the apparatus electronic circuitry and hardware; a tag apparatus power supply, the apparatus power supply coupled to and adapted to power the apparatus electronic circuitry and hardware; and a tag apparatus housing, the tag apparatus housing comprising a tag apparatus exterior and a tag apparatus interior, the tag apparatus interior containing the tag apparatus software, the tag apparatus power supply, and at least some of the tag apparatus electronic circuitry and hardware; wherein the tag apparatus exterior comprises a clamp apparatus frame adapted to be secured adjacent an umbilical cord of a newborn baby when the umbilical cord is clamped by an umbilical cord clamp; wherein the apparatus electronic circuitry and hardware are adapted to operate as a wireless tag that is adapted to be wirelessly read by wireless tag reader comprising a wireless transceiver; wherein the wireless tag reader is adapted to be communicate to a server managing location data and status data applicable to the wireless tag; and wherein the tag tamper-evident switch is secured by the tag apparatus housing, is exposed in part to the tag apparatus exterior, is coupled to the tag apparatus electronic circuitry within the interior, and is adapted to be activated, deactivated, triggered, or tripped by efforts to tamper with the wireless tag or the umbilical cord clamp;

In an exemplary embodiment, the method further may be adapted for the safety of a newborn, security of a newborn, and/or notification of a participant, in which the method comprises providing an apparatus adapted for interaction with the participant, in which the apparatus may be configured in accordance with the first aspect of the invention; configuring the apparatus to interact within the system; configuring the apparatus to interact with the participant; enabling the apparatus to interact with the participant; and adapting the apparatus to electronically process status data, identity data, location data, patient data (e.g., blood pressure, pulse, $O_2$, etc.) configuration data, audio data, video data, or a combination thereof, of an interaction of the apparatus with the participant.

Further aspects of the invention are set forth herein. The details of exemplary embodiments of the invention are set forth in the accompanying drawings and the description below. Other features, objects, and advantages of the invention will be apparent from the description and drawings, and from the claims.

BRIEF DESCRIPTION OF THE DRAWINGS

By reference to the appended drawings, which illustrate exemplary embodiments of this invention, the detailed description provided below explains in detail various features, advantages, and aspects of this invention. As such, features of this invention can be more clearly understood from the following detailed description considered in conjunction with the following drawings, in which the same reference numerals denote the same, similar, or comparable elements throughout. The exemplary embodiments illustrated in the drawings are not necessarily to scale or to shape and are not to be considered limiting of its scope, for the invention may admit to other equally effective embodiments having differing combinations of features, as set forth in the accompanying claims.

DETAILED DESCRIPTION OF THE EMBODIMENTS

Figure 1A:
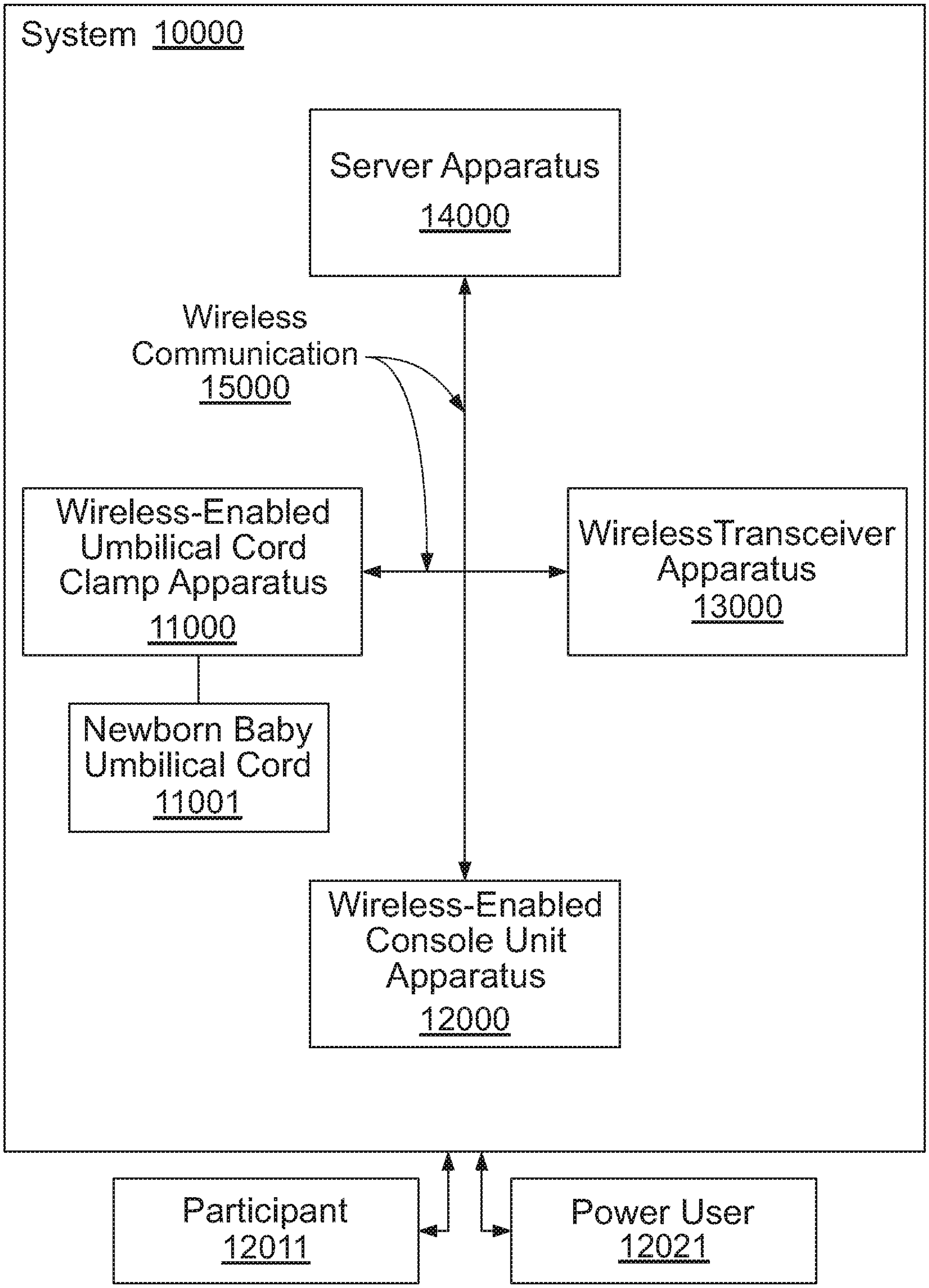
FIG. 1A shows a block diagram of an exemplary embodiment of a system, according to aspects of the invention.

The invention relates to systems, methods, and apparatus involving components that may be combined in multiple ways and may include one or more of a wireless-enabled umbilical cord clamp and/or clamp tag, a wireless transceiver, a wireless-enabled console unit, and/or a server, adapted to operate within a wirelessly-networked environment, such as a hospital, for protection identification, and tracking of newborns. As used herein the term "wireless-enabled umbilical cord clamp" means any umbilical cord clamping mechanism that is used in conjunction with the clamp tag or wireless tag of the present application as described herein.

The invention is directed to systems, methods, and apparatus involving a platform and an assembly and/or an apparatus adapted to provide a wireless monitoring system for the safety of newborn babies. In an exemplary embodiment of the invention, the apparatus embodies a wireless-enabled umbilical cord clamp apparatus adapted to function within a system that includes a handheld console, such as a smartphone or tablet computer. The apparatus may be adapted to operate as an umbilical cord clamp with an integrated or attachable configurable wireless tag having electronics, such as, a tamper-evident switch and a transceiver, and optionally a camera, a display, a microphone, a speaker, buttons, coupled to and controlled by a processor, with the apparatus adapted to be connectable to the monitoring platform, such as connectable to a data server or system, in a networked environment. The invention may be able to interface with an electronic medical record (EMR) system as well as other electronic systems such as close-captioned television (CCTV) monitoring systems and provide access (e.g., administrator) control to said systems. In some embodiments, the console may be wired and connectable to a fixed location, such as a workstation or desktop computer operating a browser or desktop app, while in other embodiments, the console may include an internal chargeable battery and a radio-frequency transceiver, so that the console may be wireless and portable, such as a smartphone or tablet computer, cither as a purpose-dedicated device, or as a software-configured device configured for that purpose.

Exemplary Embodiments of a System

In a hospital setting according to the present invention, immediately after a newborn baby is born, hospital staff use a wireless-enabled umbilical cord clamp to clamp an umbilical cord of the newborn baby, to stop blood from flowing within the umbilical cord, and then cut the umbilical cord of the newborn baby, with the clamp between the cut and the newborn to stop the umbilical cord from bleeding out from the newborn. The wireless-enabled umbilical cord clamp includes a wireless tag, either integrated into the clamp, or attachable to the clamp, and the wireless tag includes a processor, sensors, a power supply, and wireless communication circuitry to enable wireless programming and communication to and from the clamp, so that shortly after the newborn is born, the hospital staff may program the clamp apparatus and/or tag to identify the newborn and to monitor and track the newborn within the hospital. The wireless-enabled umbilical cord clamp is secured to the newborn's umbilical cord in a fashion that prevents the clamp from being tampered with or removed without triggering an alert or an alarm within the monitoring system, which may indicate an attempted unauthorized removal of the baby.

In a wirelessly-networked hospital environment according to an embodiment of the present invention, the hospital includes at least one wireless transceiver that may send and receive wireless signals in communication with the wireless-enabled umbilical cord clamp, and preferably includes a matrix of wireless transceivers distributed and mapped throughout the relevant portions of the hospital. The matrix may be mapped, for example, to relevant exit doors, hallway doors, room doors, staircases, elevators, windows, rooms, etc., and couple to such doors and to relevant lights, cameras, alarms, strobes, etc. The hospital's wireless system transceiver(s) may comprise, or communicate with, a wireless router (e.g., a Wi-Fi® router, a Bluetooth® router, a Bluetooth-Low-Energy® (BLER) router, a Bluetooth® beacon, BLE® beacon, and/or Near-Field-Communication (NFC) transceiver, beacon, or router) and/or a wireless-enabled console unit, such as a wireless-enabled desktop computer at a nurse station, and/or a nurse's handheld computing device. The wireless system transceiver may comprise and/or communicate with a system server that compiles and coordinates the data and content relative to the status of each wireless-enabled umbilical cord clamp, each wireless system transceiver, and each wireless-enabled console unit, in use and/or active within the system. The system server may communicate within the system using signals over either wired lines, such as connected to wireless routers, or over a wireless transceiver data transfer module directly integrated into or with the server. In some embodiments, a nurse's handheld wireless-enabled console itself may function as the system server.

The wireless-enabled umbilical cord clamp apparatus includes a radio-frequency identification (RFID) transceiver that allows hospital staff to track, record, and document interactions with the newborn as a patient of the hospital, such as for monitoring, moving, feeding, treating, securing, and caring for the newborn. In particular, the clamp transceiver may communicate (i.e., "ping") periodically (e.g., every 5, 10, 20, or 30 seconds, etc.) a wireless system transceiver, or matrix of wireless system transceivers, in communication with a system server and console units, to update the clamp's status. Updates to the clamp status may include, for example, the status of the clamp's integrity (e.g., has the clamp been opened or removed, triggering an alert or an alarm indicative of the possibility that an abductor is removing the clamp to abduct the newborn baby without the clamp being used to track the newborn during the abduction); the status of the clamp's battery strength and remaining power supply (e.g., does the clamp need to be recharged); and the status of the clamp's location (e.g., where is the clamp within the hospital, and has the clamp moved from an approved or designated location). Within the wirelessly-networked hospital environment, the clamp location may be determined by, for instance, triangulation among system transceivers, or comparisons of relative signal strengths from the clamp tag transceiver to one or more system transceivers.

In some embodiments, the clamp tag may use a wireless transmitter, instead of a transceiver, if the tag is designed only to transmit signals and not to receive signals, such as in low-cost, single-use disposable devices and apparatus. In some embodiments, a transceiver may be adapted or configured as a data transfer module or data transfer device that is restricted to transmitting only. If the tag uses only a transmitter, or is adapted only to transmit, the tag would operate independently of the system components, pushing information to the system, without the system influencing operation of the tag, with all programming of the data done elsewhere within the system, such as on the nurse's console or at the server, based a unique identification (ID) of the tag.

Further, in some embodiments, the clamp tag may operate as part of a mobile ad-hoc network. In some embodiments, the clamp tag acts as a wireless ad-hoc network node. Such a node may connect with one or more base station(s) and access point(s) rather than hop-by-hop forwarding. The decentralized nature of wireless ad hoc networks makes them suitable for a variety of applications including the real time location tracking features of the embodiments of the present application.

In some embodiments, the tag would operate and transmit only once the tag is activated by the closure of a clamp, such as to avoid consumption of electrical power and save battery reserves, in which closure of the clamp may complete or close a circuit required for electricity to flow within the tag. If the tag experiences a drop in power below a threshold power level, the tag may 'wake up' and transmit a low-power alert. If the tag is tampered with, such as the clamp being opened, the circuit would open, the tag would cease to operate, and the system immediately would detect a failure of the tag to ping or "check in" with the system at the tag's location last recorded seconds earlier. The system would prompt an alert, an alarm, a console notification, and/or a door lockdown, depending on the tag's status or location, upon detecting the tag's failure to check in. In some embodiments, the tag may have a bar code or other ID that allows the system to register the tag, the tag unique ID, and/or tag identity within the system without the tag being electrically active or electronically activated. In some embodiments, the tag temporarily may be powered and made electrically active or electronically activated, by temporarily closing the clamp to close the circuit to allow the nurse's console to read the tag without the clamp being closed on and attached to an umbilical cord yet, with the clamp being able to be reopened after temporarily being closed. In some embodiments, the tag identity would be entered into the system first when the tag is made electrically active or electronically activated upon closure of the clamp on an umbilical cord, with the nurse using the nurse's console to wirelessly read and associate the tag ID with the newborn baby in the system.

The hospital staff may use the status data received from an active (or activated) wireless-enabled umbilical cord clamp to monitor the location, security, treatment, and/or health of the newborn baby. For instance, each time the newborn is fed or changed, the clamp's RFID may be read and/or scanned by a nurse's console unit to document the activity. In some embodiments, the clamp may warn the hospital staff of potential changes to the newborn's health, such as if the newborn undesirably rolls or is placed onto its stomach for a time that exceeds a set threshold, as measured by a potential sudden drop in RFID signal strength in the clamp without a change in location, potentially indicative of the baby being on top of the clamp and impeding the clamp's RFID signal strength. In some embodiments, the clamp may include a sensor, such as a pressure sensor, an $O_2$ sensor, a weight sensor, a force sensor, an accelerometer, a moisture sensor, a temperature sensor, a light senor, and/or an audio sensor that may provide the system with status data, which may alert the hospital staff to potentially dangerous conditions affecting the newborn, if such sensor data meet or exceed set thresholds. For instance, if the newborn requires a heat lamp to maintain a desired ambient temperature, a temperature sensor in the clamp may alert the hospital staff if the ambient temperature rises or falls outside the desired temperature range, potentially indicating that the heat lamp is malfunctioning or that someone maladjusted the heat lamp. Hospital staff may receive an alert or an alarm and take appropriate action to remedy a cause that triggered the alert or the alarm, and when appropriate, reset the clamp, the alert, and/or the alarm upon remedying the cause.

Once the newborn is ready to leave the hospital with an approved adult, the hospital staff may set, deactivate, and/or inactivate the clamp within the system, such as at the tag itself, at the console, or at the server, to avoid triggering a removal alert or alarm and possible abduction warning, and then remove the clamp. By the time the newborn is ready to leave the hospital, the newborn's umbilical cord will have closed, sealed, and healed, such that the clamp no longer is needed to prevent the umbilical cord from bleeding. The used wireless-enabled umbilical cord clamp then may be recycled, if disposable as a single-use device, or disinfected and/or sterilized and prepared for reuse, if constructed and designed as a durable, disinfectable/sterilizable, rechargeable, reprogrammable, reusable, multi-use device.

Whether constructed and designed as a single-use or multi-use device, the wireless-enabled umbilical cord clamp preferably would be waterproof (e.g., subject to submersion when bathing a baby wearing the clamp) and disinfectable/sterilizable by hospital-grade topical disinfectants (e.g., alcohol swabs or sprays), to survive and function properly during the baby's stay and treatment in the hospital. Similarly, so that the baby tolerates wearing the clamp, the clamp needs to be non-irritating in materials, such as to no cause any allergic reaction (e.g. hypoallergenic), contact dermatitis, or other skin ailment, and configuration (e.g., preferably low-profile, with no sharp edges or pointy corners). If designed and manufactured as a disposable, single-use device, the manufacturing costs preferably would be lower than for a reusable, multi-use device, such that a reusable, multi-use device may include more features, functions, and components (e.g., sensors) that increase the per-device costs, which may include licenses for relevant hardware, software, and/or intellectual property to make, sell, and/or use the device.

In preferred embodiments, the manufacturing costs of a single-use, the units would be as small and light-weight as practicable, weighing about 12 grams or less (e.g., preferably 5-6 grams), to avoid strain on the healing umbilical cord or the baby. An exemplary clamp may have a clamp transceiver tag with dimensions of about 34 mm long, about 29 mm wide, and about 5 mm height. An exemplary embodiment would be made of hypoallergenic, biocompatible materials that are rigid, durable, somewhat flexible, and solvent-resistant, such as compositions, combinations, polymers, and/or co-polymers of latex, lead, DEHP, polycarbonate, trimethyl carbonate, polyethylene, polypropylene, polyvinylchloride, polytetrafluoroethylene, stainless steel, alumina, aluminum/aluminium, cobalt-chromium alloy, and silicone, among others.

In some embodiments, the power source may include a battery having a functional battery life permitting many hours of use, such as 12, 24, 36, 48, or 72 hours. In other embodiments, the battery life may last months or years depending on usage and battery type. In preferred embodiments, the power source would include a battery having a functional battery life of at least 96 hours. The power supply preferably would last the entire duration of a typical newborn's hospital stay in the U.S. In the U.S., mothers and newborns typically are discharged from the hospital within two days of a vaginal delivery, and in three days of a delivery by Caesarcan section. A battery life of about 96 hours may be achieved, for example, with a silver oxide "coin" battery beginning with 200 mAh power if the average power consumption is low enough, as low as 2.08 mA. In an embodiment with an approximate average power consumption of about 10.34 mA, a battery beginning with about 1000 mAh would have a battery life of about 96.7 hours. The clamp processor may detect or measure remaining battery power, such as using a circuit activated at a low power. When the remaining battery power nears a functional minimum power level, the clamp may detect this low battery level and send a "low battery" alert to the system.

In preferred embodiments, the clamp transceiver, such as a BLE transceiver, would emit a signal having a functional signal strength that is readable from at least about 10 feet (about 3.1 meters), and preferably longer (e.g., 20-30 feet), away from the clamp, to increase effectiveness of security precautions, such as locking a nursery door if an activated clamp set to "no exit" comes within a minimum safety distance (e.g., about 10 feet) of the nursery door. In some embodiments, an effective read range may be at least 30 feet (or more), such that the system detects an approach of an approaching tag from at least 30 feet away from an exit door, and locks the exit door when the approaching tag gets within about 10 feet of the exit door. An exemplary BLE transceiver may be integrated with a processor on a single printed circuit board (PCB), or coupled to the processor separately from the processor's PCB.

In preferred embodiments, the clamp would be applied easily by trained hospital staff, and yet be able to properly detect tampering or other efforts to disable, disengage, or remove the clamp without authorization and prior deactivation of the clamp, and trigger an alarm or an alert as the result of such unauthorized activities. An exemplary tamper detection device may include, for instance, an enclosed microswitch, pressure sensor switch, or button switch, having an enclosure that limits access, activation, or deactivation, of the tamper detection device without opening the clamp. In preferred embodiments, the clamp would be suitable for use with a wide range of newborn body types and cord conditions, possibly having an alternative clamp configuration for each specific cord condition or newborn born body type.

In some embodiments of the present invention, a system is provided that comprises a hospital security platform that connects the nurse's interface with EMR access to the security system in a networked environment, which may include connections between the building doors that may be electronically and remotely locked and unlocked as well as the ability to notify on site staff and send electronic alerts to dedicated or remote devices. The platform and system may provide a dashboard of, for instance, user activity, tag activity, tag status, and console status data.

Drawings of Exemplary Embodiments of the Invention

Referring to the Figures, a clamp apparatus or a clamp assembly may comprise a mechanical clamping mechanism, operable to clamp an umbilical cord of a newborn baby, and a computing device as an integrated tag or an attachable tag, operable to wirelessly communicate to a wireless-enabled console, a wireless-enabled checkpoint, and/or a server. The clamp apparatus or clamp assembly may be connectable to a security platform via a networked environment, and may comprise part of and/or communicate with an electronic medical records (EMR) media server platform or system, which may include a data system, including at least one server and at least one database, and a network system, including computing devices in communication with each other via network connections.

Referring to FIG. 1A, FIG. 1A shows a block diagram of an exemplary system 10000 adapted to monitor the safety and location of a newborn baby. The system 10000 may comprise a wireless-enabled umbilical cord clamp apparatus 11000, adapted to mechanically clamp an umbilical cord 11001 of a newborn baby; a wireless-enabled console unit apparatus 12000, adapted to interact with the clamp apparatus 11000; a wireless transceiver apparatus 13000, adapted to wirelessly interact with the clamp apparatus 11000; and a server apparatus 14000, adapted to manage and maintain data, rules, and interaction within the system 10000. Components of the system 10000 may communicate using wireless communication 15000 within the system 10000, as well as wired communication between components when wiring is provided. The system 10000 may be used by users such as a participant 12011, who may be a nurse, and a power user 12021, who may be a supervising nurse or information-technology (IT) resource employee responsible for configuring, managing, and supervising the system 10000 and/or the nurse participant 12011.

The clamp apparatus 11000 may comprise an umbilical cord clamp and an integrated wireless tag or an attachable wireless tag. The console apparatus 12000 may comprise a computing device, such as fixed-location desktop computer or nurse's workstation, or a mobile computer or other configurable device, like a laptop computer, a tablet computer, or a mobile smart device, such as a mobile smartphone. The transceiver apparatus 13000 may comprise a wireless receiver adapted to receive wireless signals from the clamp apparatus 11000, and a wired or wireless transmitter to communicate clamp status data to the console 12000 or the server 14000. For instance, the transceiver apparatus 13000 may include a wireless BLE reader adjacent a doorway, such as an entrance or an exit, adapted to detect and report BLE signals emitted by the clamp apparatus 11000. Transceiver apparatus 13000 preferably is one of many such signal readers forming a matrix of signal detection within a hospital for granular location determination. The server 14000 may comprise a local server, a local area network (LAN) server, a wide-area network (WAN) server, a cloud-based network server, a further use of the console 12000, or a combination thereof. As explained elsewhere, the system 10000 may be a part of a larger system, such as a hospital security platform and/or an EMR platform or system.

Figure 1B:
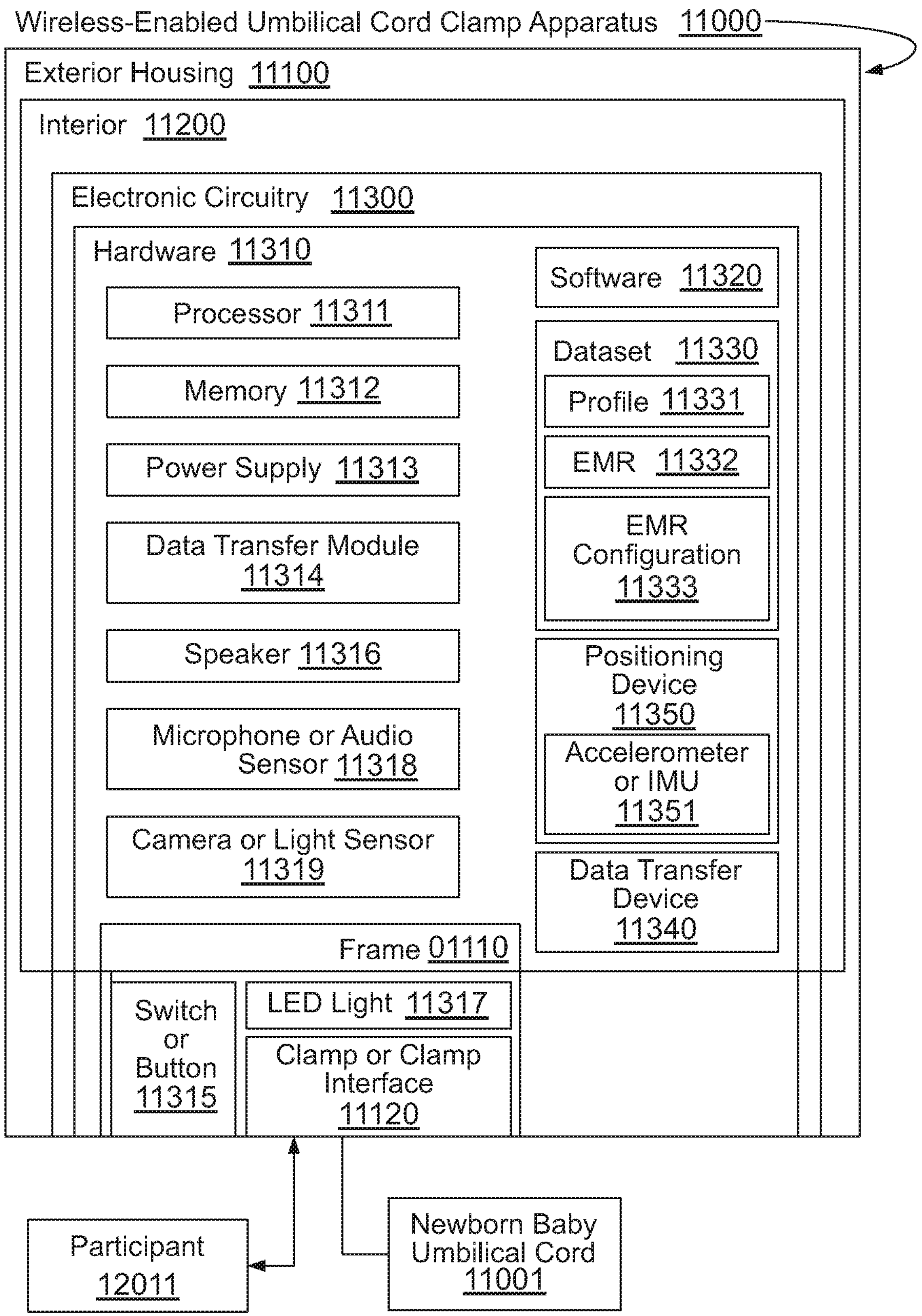
FIG. 1B shows a block diagram of an exemplary embodiment of a wireless-enabled clamp or clamp tag apparatus, according to aspects of the invention.

Referring to FIG. 1B, FIG. 1B shows a block diagram of an exemplary clamp apparatus 11000 adapted for use in system 10000. The clamp apparatus 11000 may be a self-contained cord clamp, if sufficient computing power and memory are integrated therein, or the clamp apparatus 11000 may comprise an assembly of an umbilical cord clamp and a wireless tag, in which the wireless tag is adapted interoperate with the umbilical cord clamp, such as to permit detection of efforts to tamper with or remove the clamp. The present invention envisions that components of the system 10000 may be sold separately, and the present invention encompasses, as a separate embodiment of the present invention, a non-integrated wireless tag attachable to a conventional umbilical cord clamp. The apparatus 11000 may be configured for unidirectional or bidirectional communication adapted for use by participants 12011. As depicted, the apparatus 11000 comprises a wireless-enabled clamp apparatus, having an exterior housing 11100, such as that of a combination of clamps 90000, in FIG. 9A to FIG. 9D, and wireless tags 100000 or 110000, in FIG. 10A to FIG. 11D. Exterior housing 11100 may define an interior compartment 11200 containing electronic circuitry 11300. The housing 11100 may include a frame 11110. The exterior housing 11100 and frame 11110 may be made from a suitably durable material, such as polycarbonate or other biocompatible material.

The electronic circuitry 11300 includes an integrated electronic hardware system 11310 and an integrated software operating system 11320 stored and executable on the integrated electronic hardware system 11310. The software 11320 may include, for example, firmware, an operating system, applications, drivers, libraries, and application programming interfaces. The electronic software 11320 may be stored in the electronic circuitry 11300 and hardware 11310 and may be adapted to enable, drive, and control the electronic circuitry 11300 and hardware 11310. The integrated electronic hardware system 11310 may include, for instance, one or more printed circuit boards ("PCB"), such as a motherboard, integrating an internal processor 11311 coupled to an internal memory 11312, an internal power source 11313, an integrated data transfer module 11314, and an integrated switch or button input device 11315, and interoperable with software 11320, a dataset 11330, and a data transfer device 11340.

Other optional integrated components may include an integrated speaker 11316 (such as to beep as an alarm), an integrated illumination device 11317 (such as a light-emitting-diode (LED) light to flash as an alert or an alarm), an integrated microphone or audio sensor 11318, and an integrated camera 11319. The optional components presumably would be integrated into a more-expensive, reusable apparatus, whereas fewer components presumably would be integrated into a less-expensive, single-use apparatus.

Button or switch 11315 may be adapted to activate the apparatus 11000 and to detect efforts to tamper with and/or remove the apparatus 11000, such as in an attempt to abduct a newborn baby. Switch 11315 may comprise, for instance, a switch 120000 depicted in FIG. 12A to FIG. 12C. In some embodiments, a switch or button 11315 might include a locking button that is readily depressed by a finger, but once depressed, locks, and remains locked in the depressed position and activated state, until and requiring release using a special-purpose tool or key, operable from without the exterior housing 11100. If a button 11315 locks to keep the clamp apparatus 11000 activated, a separate tamper-evident switch 11315 may be used to detect tampering, such that tampering readily activates or deactivates the separate tamper-evident switch 11315, while a locking activation button keeps the clamp apparatus 11000 active and transmitting within the system 10000 to allow the system 10000 to track and find a tampered-with or removed clamp apparatus 11000.

In other embodiments, button or switch 11315 may be a force sensing resistor (FSRs) which are pressure-sensitive components that change their resistance based on applied force making such switches suitable for detecting pressure or touch, piezo sensors that generate an electrical signal when subjected to mechanical stress (such as pressure or vibration), capacitive touch systems that detect changes in capacitance caused by proximity or touch, pressure-sensitive mats which are similar to the concept of pressure-sensitive alarm pads which encompass mats using layers of conductive material (e.g., silver foil) separated by insulating material (e.g., neoprene), or smart fabrics/textiles which are conductive fabrics and/or textiles embedded with sensors can detect pressure, touch, and/or movement.

Remember that the choice of alternative depends on factors such as sensitivity, durability, cost, and the specific application requirements.

The processor 11311 may include, dependent on the needs of the integrated components, a central processor unit ("CPU"), a graphics processor (i.e., a graphics card or video card), or combination thereof. The software 11320 and the hardware 11310 may be adapted to enable a participant 12011 and/or a power user 12021 to set up the apparatus 11000 from or by the console 12000, such as to create in the software 11320 and store in the memory 11312 a dataset 11330 including a first profile 11331 identifying a first newborn baby, and to download, install, select, and run an EMR app 11332 and an EMR app configuration 11333 for, and compatible with, a configurable app, such as EMR app 11333.

In some more-expensive embodiments, the hardware 11310 further may include a portable, small or mini display as the illumination device 11317, similar to the display of a smartwatch, and wherein the software 11320 may be adapted to render on the display 11317, for instance, a settings menu, an audiovisual file, an image file, on-screen text, on-screen text-entry icons, or any combination thereof. In some embodiments, the display 11320 may be touch-sensitive. Although the display 11320 may emit light, such as using a backlight or illuminated pixels (e.g., such as in displays in which each pixel is an organic light emitting diode ("OLED")), the hardware 11310 further may include a simple illumination device adapted to illuminate at least a portion of the exterior housing 11100. For instance, the illumination device 11317 may include a light emitting diode ("LED") adapted to illuminate a portion of the exterior housing 11100 surrounding the switch or button 11315. An LED light 11317 may indicate a status of the apparatus 11000, such as an off/no light indicating no alert or alarm, flashing white light indicating pinging signal transmissions, flashing green light indicating programming mode, flashing yellow light indicating a low-battery warning, flashing red light indicating very-low-battery alert, and non-flashing red light indicating an alarm, such as a perimeter violation alarm.

The apparatus 11000 includes a data transfer device 11340 adapted to interoperate with the electronic circuitry 11210. The data transfer device 11340 may include at least one wireless communication module, such as a wireless transmitter or wireless transceiver, and possibly one or more wired communication modules and/or device, as explained in further detail relative to FIG. 3. For instance, a wire-based data transfer device might be used to recharge the apparatus 11000.

As depicted, the apparatus 11000 includes a positioning device 11350 adapted to generate positioning data for use in determining the position, orientation, movement, motion, and/or perspective of apparatus 11000. In some embodiments, this is done in real-time via a combination of hardware, software, and communication technologies to determine and relay the real-time location of tagged items or people within a defined area of interest. In some embodiments, the positioning device 11350 is "non-computative" and comprises the data transfer device 11340 that is adapted to transmit the apparatus-outbound wireless signals used to determine the location of the apparatus 11000 within the system 10000. In more sophisticated and complicated embodiments of apparatus 11000, such as an embodiment described above that is reminiscent of a smartwatch, the positioning device 11350 may comprise other technology components, mentioned below, and also may be called a position measurement device. The positioning device 11350 may generate or be used to generate data about the relative position of the apparatus 11000, but the positioning device 11350 does not "position" the apparatus, in the sense that a gimble might "position" or a tripod might support the apparatus in a fixed position.

An "active" or "computative" positioning device 11350 may include a global positioning system (GPS) receiver and/or GPS module, from which an "absolute" position relative to Earth might be measured and calculated locally within the apparatus 11000. In some embodiments, the importance of the positioning device 11350 for the apparatus 11000 may relate more to the relative point of view of the apparatus 11000 within the system 10000 (such as a location within a hospital), than to the absolute location of the apparatus 11000. Exemplary positioning devices 11350 may include a gyroscope, an infrared (IR) sensor, an accelerometer, an inertia motion unit (IMU) 11351, and/or other sensor that may be adapted to detect on-stage beacons or other tracking devices (see FIG. 5) that emit signals suitable for triangulation of a location of the apparatus 11000. In some embodiments, a sensor may comprise a sensor-transmitter pair (e.g., light detection and ranging ("LiDAR"), or laser detection and ranging ("LaDAR")) for active range determinations locally. Alternatively, the software 11320 may be programed to recognize in-view artifacts (e.g., identifiable background objects, like a crib, to identify if a newborn is leaving or has left the newborn's crib), captured in the video data by the camera 11319, using machine vision and/or artificial intelligence ("AI") for determination of the location of the apparatus 11000, such as using triangulation or comparable AI calculation.

Various data settings of the apparatus 11000 may include creating the first profile 11331 to include, for example, entering a first baby name of the newborn to whom the clamp apparatus 11000 was attached, a first participant name of the first participant 12011 or power use 12021 (e.g., the nurse who attached the clamp apparatus), or a biographical event (e.g., a birthdate), and storing a first face image of a face of the newborn or the first participant 12011 or power use 12021, or an image of the newborn's mother. The camera 11319 and the software 11320 may be adapted to recognize the face of the first participant 12011 or power use 12021 based on a comparison with the first face image. The user may associate the first face image with the user's profile for inclusion in the user's postings on the online EMR platform or EMR media system. Moreover, the configuration 11333 may be specific to the user's profile and may be configured to load automatically upon recognizing the face of the first participant 12011 or power use 12021 within a specified distance of the apparatus 11000.

Among other possible variations, the software 11320 may be further adapted to enable the power user 12021 to select one of a plurality of languages programmed into the software 11320; to select one of a plurality of settings programmed into the software 11320; to set up the first profile by entering first profile parameters including a first performance, a first role, a first position, a first location, a first event, etc., or any combination thereof, relative to the first participant and/or first biographical event; and to configure the software 11320 to adjust interaction parameters based on the first profile parameters entered.

Technical variations may include, for example, having the camera 11329 and the software 11320 adapted to measure ambient light, motion, or both, such that the apparatus 11000 may be adapted to alternate between a less-active state, an inactive state, and an active state based on measuring a presence or an absence of a minimum threshold of ambient light, motion, or both.

Figure 1C:
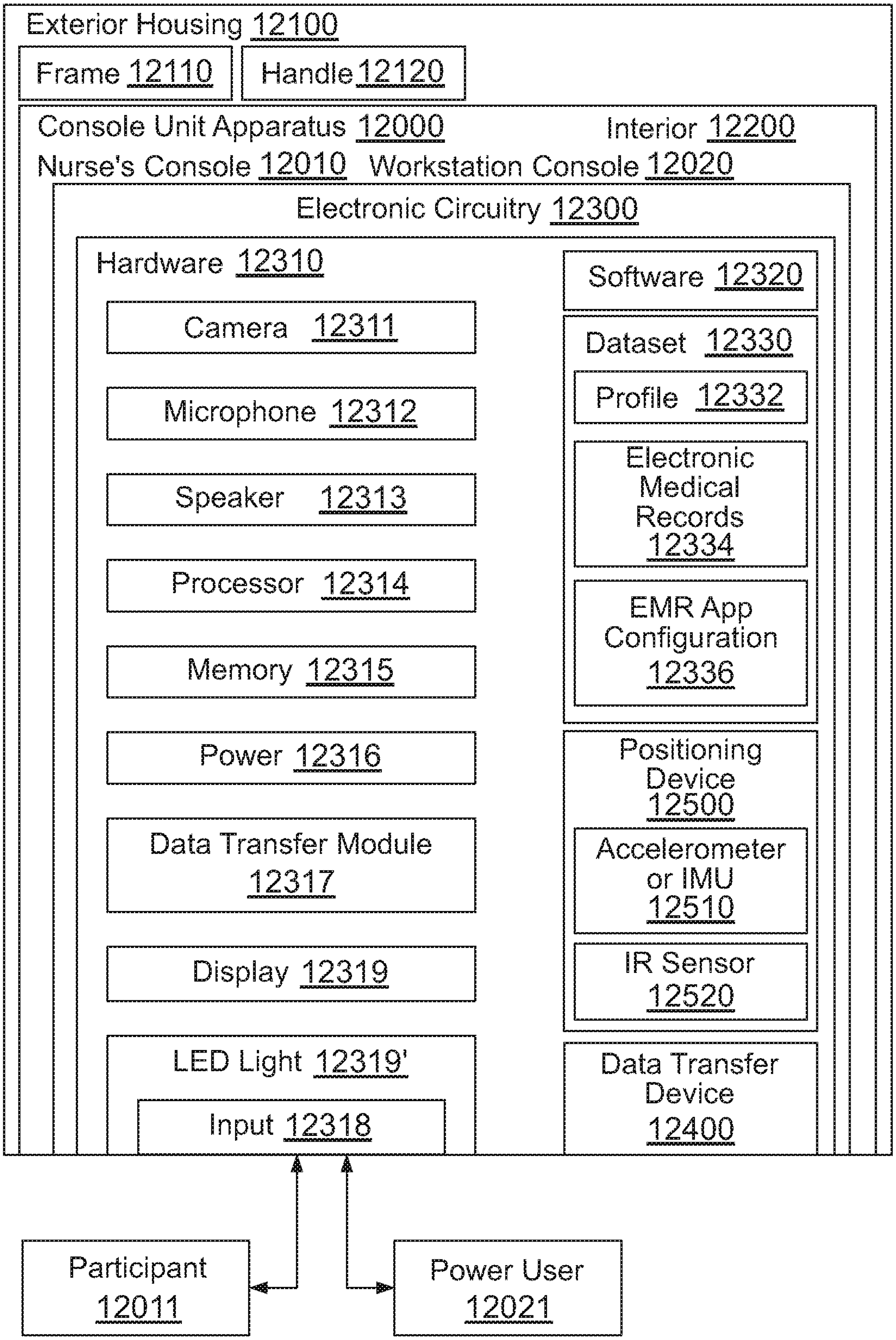
FIG. 1C shows a block diagram of an exemplary embodiment of a console apparatus, according to aspects of the invention.
Figure 3:
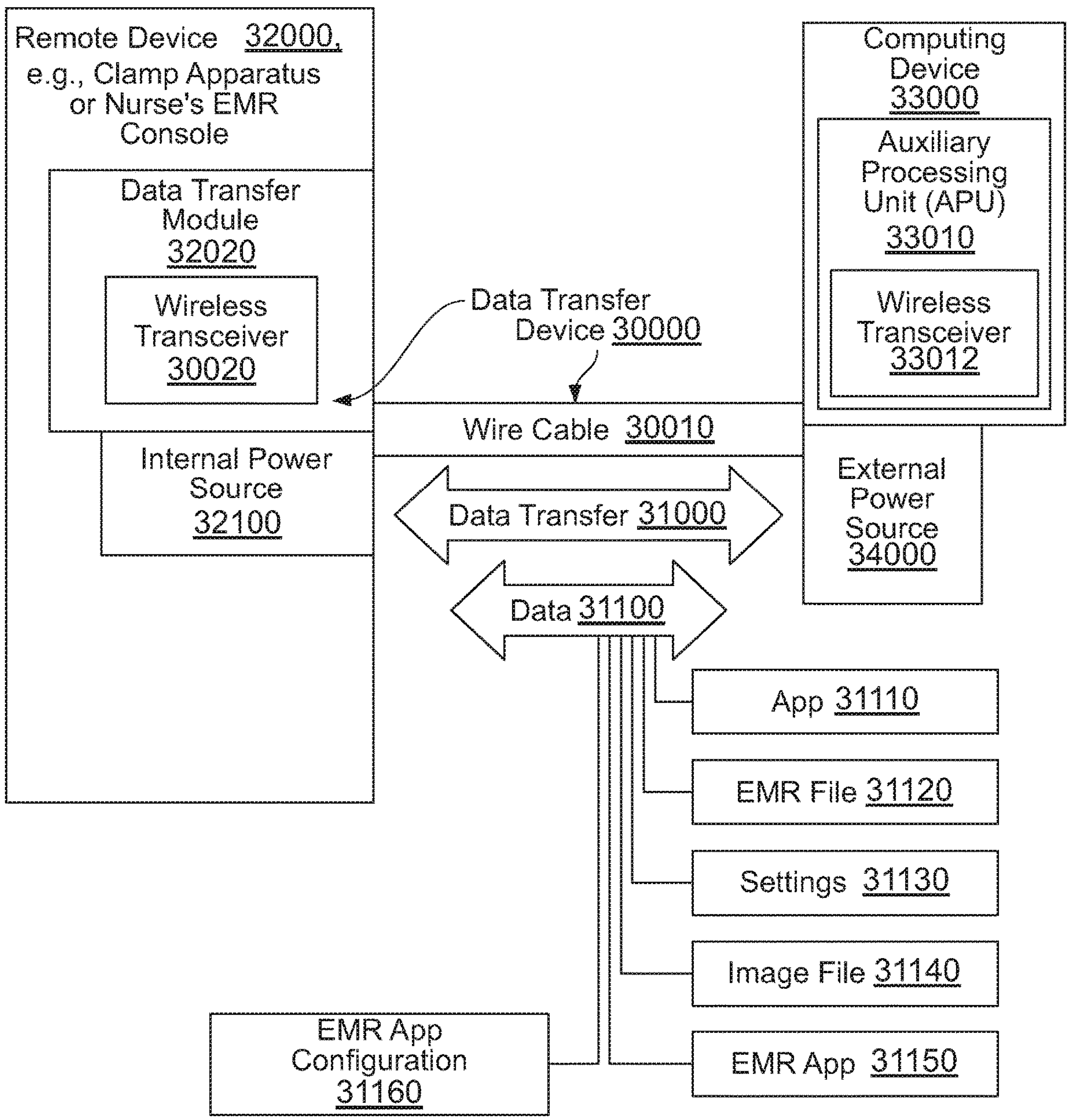
FIG. 3 shows a block diagram of an exemplary embodiment of an operation of the apparatus of the present invention, according to aspects of the invention.

Referring to FIG. 1C, FIG. 1C shows a block diagram of a console unit apparatus 12000 adapted to comprise and/or operate as a nurse's console 12010, and/or a workstation console 12020, or other configurable device like a laptop computer, a tablet computer, or a mobile smart device, such as a mobile smartphone. The apparatus 12000 may be self-contained, if sufficient computing power and memory are integrated therein (e.g., in a smartphone), or the apparatus 12000 may comprise and/or interoperate with a separate computing device, as depicted in FIG. 3 et seq. The apparatus 12000 may be configured for interactive communication adapted for use by participants 12011 in a hospital environment. As explained below, the apparatus 12000 may be a part of a larger system, such as an EMR platform and/or a hospital security platform or system. As depicted, the apparatus 12000 comprises a nurse's console 12010 or a workstation console 12020, having an exterior housing 12100, defining and having an interior compartment 12200 containing electronic circuitry 12300. The housing 12100 may include a frame 12110, and an optional handle 12120. The exterior housing 12100 and frame 12110 may be made of suitably durable materials as conventionally used in the construction of smartphones, tablets, and laptops.

The electronic circuitry 12300 includes an integrated electronic hardware system 12310 and an integrated software operating system 12320 stored and executable on the integrated electronic hardware system 12310. The software 12320 may include, for example, firmware, an operating system, applications, drivers, libraries, and application programming interfaces. The electronic software 12320 may be stored in the electronic circuitry 12300 and hardware 12310 and may be adapted to enable, drive, and control the electronic circuitry 12300 and hardware 12310. The integrated electronic hardware system 12310 may include, for instance, one or more printed circuit boards ("PCB"), such as a motherboard, integrating an assortment of optional components, such as an integrated camera 12311, an integrated microphone 12312, and an integrated speaker 12313, that are coupled to an internal processor 12314, coupled to an internal memory 12315, an internal power source 12316, an integrated data transfer module 12317, interoperable with a data transfer device 12400, and at least one integrated input device 12318 (e.g., button, switch, dial, slider, keypad, keyboard, joystick, touchpad, touchscreen, fingerprint sensor, camera, photosensor, infrared sensor, microphone, audio sensor, motion sensor, gyroscope, accelerometer, inertia motion unit ("IMU"), etc.) operable from without the exterior housing 12100. The processor 12314 may include, dependent on the needs of the components, a central processor unit ("CPU"), a graphics processor (i.e., a graphics card or video card), or combination thereof. The software 12320 and the hardware 12310 may be adapted to enable a power user 12021 to set up the configurable console 12000, such as to create in the software 12320 and store in the memory 12315 a dataset 12330 including a first profile 12332 identifying a first participant 12011, and to download, install, select, and run an EMR app 12334 and an EMR app configuration 12336 for, and compatible with, a configurable app, such as EMR app 12334.

The hardware 12310 further includes a portable, medium, small or mini display 12319, such as found on a smartphone or tablet computer, and wherein the software 12320 is adapted to render on the display 12319, for instance, a settings menu, an audiovisual file, an image file, on-screen text, on-screen text-entry icons, or any combination thereof. In some embodiments, the display 12319 may be touch-sensitive. Although the display 12319 may emit light, such as using a backlight or illuminated pixels (e.g., such as in displays in which each pixel is an organic light emitting diode ("OLED")), the hardware 12310 further may include a simple illumination device 12319' adapted to illuminate at least a portion of the exterior housing 12100. For instance, the illumination device 12319' may include a light emitting diode ("LED") adapted to illuminate a portion of the exterior housing 12100, such as for use as a flashlight, or as a prompt surrounding the input button 12318. An LED light 12319' may indicate a status of the nurse's console 12010.

Various data settings of the apparatus 12000 may include creating the first profile 12332 to include, for example, entering a first participant name of the first participant 12011 or power user 12021, a name of a newborn baby, or a biographical event (e.g., a birthdate), and storing a first face image of a face of the first participant 12011 or power user 12021, or an image of the mother. The camera 12311 and the software 12320 may be adapted to recognize the face of the first participant 12011 or power user 12021 based on a comparison with the first face image. The user may associate the first face image with the user's profile for inclusion in the user's postings on the online EMR platform or EMR media system. Moreover, the EMR configuration 12336 may be specific to the user's profile and may be configured to load automatically upon recognizing the face of the first participant 12011 or power user 12021 within a specified distance of the apparatus 12000.

Among other possible variations, the software 12320 may be further adapted to enable the power user 12021 to select one of a plurality of languages programmed into the software 12320; to select one of a plurality of settings programmed into the software 12320; to set up the first profile by entering first profile parameters including a first performance, a first role, a first position, a first location, a first event, etc., or any combination thereof, relative to the first participant and/or first event; and to configure the software 12320 to adjust interaction parameters based on the first profile parameters entered.

Technical variations may include, for example, having the camera 12311 and the software 12320 adapted to measure ambient light, motion, or both, as well as measuring patient vitals (e.g., blood pressure, pulse, temperature, skin contact, etc.) such that the apparatus 12000 may be adapted to alternate between a less-active state, an inactive state, and an active state based on measuring a presence or an absence of a minimum threshold of ambient light, motion, or both.

The apparatus 12000 includes a data transfer device 12400 adapted to interoperate with the electronic circuitry 12300. The data transfer device 12400 may include at least one wireless transceiver, and possibly one or more other wired and/or wireless communication devices or modules, as explained in further detail relative to FIG. 3.

The apparatus 120000 may include a positioning device 12500 adapted to generate positioning data for use in determining the position, orientation, movement, motion, and/or perspective of console 12010. The positioning device 12500 also may comprise and be called a position measurement device. The positioning device 12500 may generate data about the relative position of the console apparatus 12000, but does not "position" the apparatus 12000, in the sense that a gimble might "position" or a tripod might support the apparatus in a fixed position. The positioning device 12500 may include a global positioning system (GPS) receiver and/or GPS module, from which an "absolute" position relative to Earth might be measured and calculated. In some embodiments, the importance of the positioning device 12500 for the apparatus 12000 may relate more to the relative location of the apparatus 12000 within the system 10000 than to the absolute location of the apparatus 12000. Exemplary positioning devices 12500 may include a gyroscope, an accelerometer, an inertia motion unit (IMU) 12510 and/or an infrared (IR) sensor 12520 or other sensor that may be adapted to detect (see FIG. 5) local, stationary beacons (e.g., wireless transceiver apparatus 13000) or other tracking devices (e.g., wireless-enabled clamp apparatus 11000) that emit signals suitable for triangulation of a location of the console 12010 relative to the other devices. In some embodiments, a sensor may comprise a sensor-transmitter pair (e.g., light detection and ranging ("LiDAR"), or laser detection and ranging ("LaDAR")) for active range determinations. Alternatively, the software 12320 may be programmed to recognize in-view artifacts (e.g., identifiable background objects, like the nurse's station), captured in the video data by the camera 12311, using machine vision and/or artificial intelligence ("AI") for determination of the location of the console 12010, such as using triangulation or comparable AI calculation.

Figure 2:
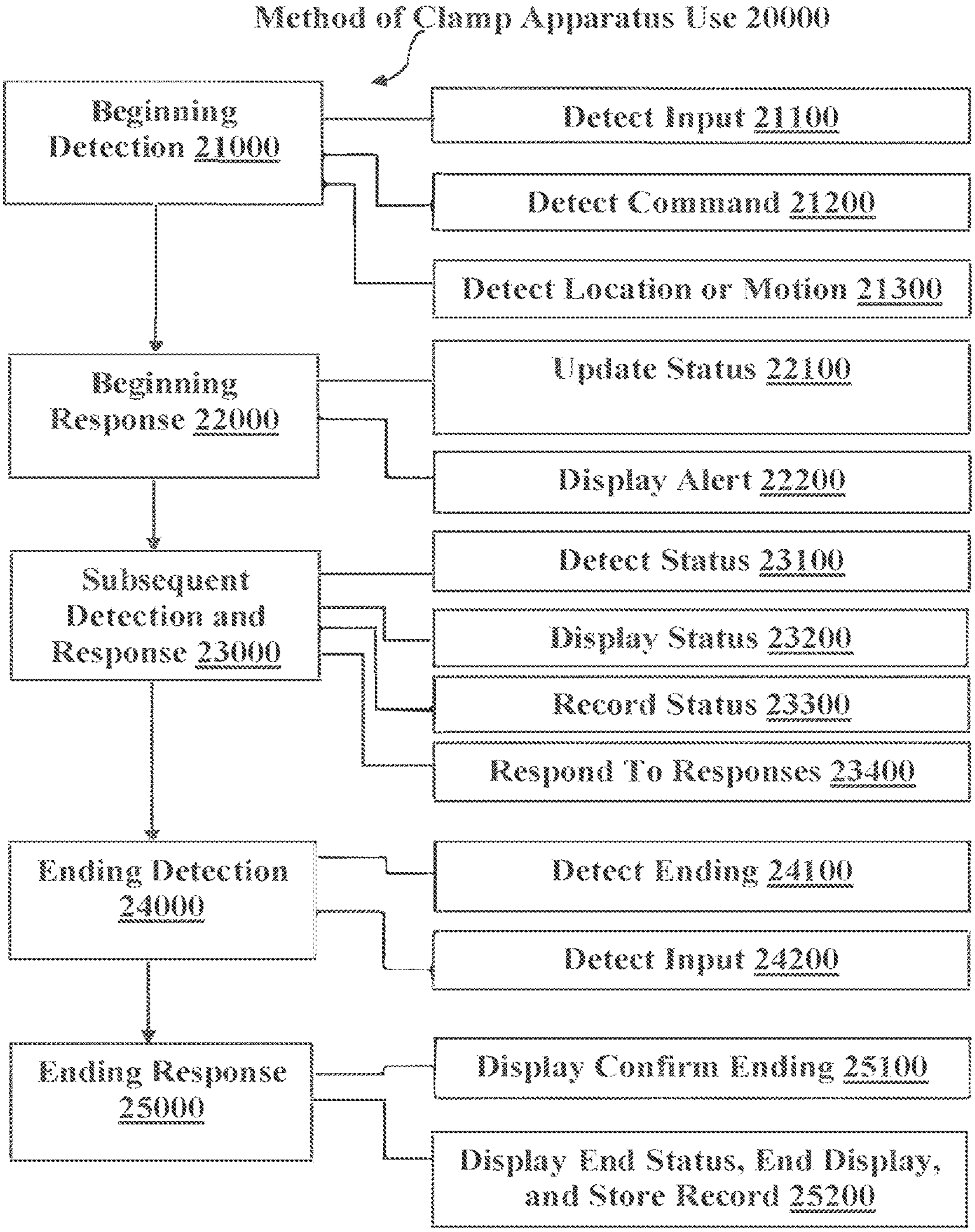
FIG. 2 shows a block diagram of an exemplary embodiment of a method of use of an exemplary apparatus, according to the prior art of the invention.

Referring to FIG. 2, FIG. 2 shows a flow diagram of an exemplary method 20000 of using a clamp apparatus 11000, such as the apparatus 11000 of FIG. 1A or FIG. 1B, according to aspects of the invention. The method 20000 may be adapted to perform, upon detecting an EMR app configuration 11333, loading a configuration beginning detection 21000, a beginning response 22000. For example, the beginning detection 21000 may include detecting the input button being activated (21100), detecting a command being provided (21200) by a nurse on console apparatus 12000, detecting a location or motion of the clamp apparatus (21300), or any combination thereof. Likewise, the beginning response 22000 may include using the console 12000 to update (22100) the status of the clamp apparatus 11000 as activated within the server 14000, and may optionally include the speaker 11316 to play audio or illumination device 11317 display lights, such as to confirm the activation. The beginning response 22000 may include using the console 12000 to display (22200) an alert, such as advising the first participant 12011 that the clamp apparatus 11000 is activated within the system 10000, or to activate the input button 11315 by closing the clamp 11120 on the newborn's umbilical cord, or both, upon detecting the beginning detection 21000. Following the beginning response 22000, the method 20000 may be adapted to perform a subsequent detection and response 23000, such as to detect (23100) updates to the status of the clamp apparatus 11000, to display (23200) an updated status of the clamp apparatus 11000 on the nurse's console 12000 (e.g., an alert if the low-battery status is indicated, or an alarm if the tamper detection status or perimeter violation detection status is indicated), to record (23300) the status update as an interaction file in the EMR app 12334 and possibly the memory 11312 or EMR configuration 11333, and in response to which, to respond (23400) to updated status or other response with the system 10000, such as by the nurse on console 12000 or from EMR app 12334. For example, a response to an alert if the low-battery status is indicated may include replacing and/or recharging (inductive charging, photoelectric charging, kinetic recharging, USB charging, etc.) the clamp apparatus 11000, whereas a response to an alarm if the tamper detection status or perimeter violation detection status is indicated may include sending signals to electronically lock perimeter doors near the last-recorded location of the clamp apparatus 11000.

The method configuration 20000 may be configured to have the software 12320 and the hardware 12310 further be adapted to enable a power user 12021 to set up the method configuration 20000 to select an ending detection 24000 and an ending response 25000 to the ending detection 24000, wherein the method 20000 further is adapted to perform the ending response 25000 upon detecting the ending detection 24000. The ending detection 24000 may include, for instance, detecting an ending (24100), such as the end of the use of the clamp apparatus 11000 upon discharge of the newborn baby from the hospital; detecting an input (24200), such as a locking input button 11315 being inactivated, or a tamper-evident switch 11315 being activated upon making a nurse-authorized opening and removal of the clamp apparatus 11000, such as to discontinue tracking of the clamp apparatus 11000, or both. The ending detection 24000 may initiate the ending response 25000 that concludes an interaction of the method 20000 with the clamp apparatus 11000 by the system 10000 via the nurse console 12000 used by the first participant 12011. The ending response 25000 may include confirming (25100) the ending in the EMR app 12334, such as using the speaker 11316 and/or 12313 to sound a deactivation chime to the first participant, or using the light 11317 to illumination a deactivation lighting pattern and/or the display 12319 to display a deactivation confirmation screen. The ending response 25000 further may include storing, updating, displaying, and recording (25200) the ending status of the interaction as an interaction file as a computer-readable file on a computer-readable storage medium, such as an EMR file 12334 in EMR app 12336. The ending response 25000 might also include connecting to the network, connecting to a EMR server 14000 or platform, and sending an alert to the power user 12021 to notify the power user 12021 that a participant 12011 has concluded interacting with the apparatus 11000 and that a file 12334 of the interaction may be available on the EMR server 14000 and/or stored in the console 12010.

Referring to FIG. 3, FIG. 3 shows a block diagram of an exemplary embodiment 30000 of the present invention specific to a data transfer device 13000. A data transfer device 30000 may be adapted to enable a data transfer 31000 between a remote device 32000, such as a clamp apparatus 11000 or an EMR console 12000, and a separate computing device 33000, such as to provide additional computing, video-capturing, video-processing, image-capturing, image-processing, data processing, communicating, networking, and/or storing capabilities, such as including an auxiliary processing unit ("APU") 33010 or a server of an EMR platform, wherein the data transfer device 30000 may be adapted to enable the remote device 32000 to communicate with and transfer electronic data 31100 to the separate computing device 32000 and to enable the separate computing device 33000 to communicate with and transfer electronic data 31100 to the remote device 32000. For example, in situations in which multiple remote devices 32000 may attempt to communicate with a backend server simultaneously from the same general location, such as while users are distributed throughout rooms in a hospital, a computing device 33000 may act as an intermediate buffer, data aggregator, network bus, cache, or router to facilitate simultaneous high-volume, high-data communication between multiple local consoles and a backend system server over the Internet. In some embodiments, the computing device 33000 may comprise a component of a matrix of wireless transceiver apparatus 13000, each of which may be adapted to serve as a beacon, a location reader, a perimeter port, a data bridge, a sub-router, a data communication range extender, or a combination thereof.

The data transfer device 30000 may include, for instance, a wire cable 30010, a wireless transceiver 30020, or both, possibly in combination with wireless transceiver 33012 of APU 33010, wherein the remote device 32000 may be enabled via a data transfer module 32020 to transfer to, or receive from, the separate computing device 33000, for example, a separate device software application 31110 and an EMR file 31120. Wired cables may include, for instance, an Ethernet cable, RJ45 cable, coaxial cable, USB cable, Thunderbolt cable, Lightning cable, HDMI cable, VGA cable, MIDI cable, etc. A wireless transceiver 30020, 33012 may comprise, for instance, a Wi-Fi transceiver; WiLAN transceiver; a Zigbee transceiver, a Z-wave transceiver, a 6LoWPAN transceiver, a Near-Field-Communication (NFC) transceiver; a Bluetooth transceiver or a Bluetooth Low Energy (BLE) transceiver; a 1G, 2G, 3G, 4G, or 5G cellular transceiver; a Long-Term Evolution (LTE) cellular transceiver, or other low-power IoT enabled technology, etc. Likewise, the separate computing device 33000 may be enabled to transfer to, or receive from, the remote device 32000, for instance, a settings dataset 31130 and an image file 31140. For example, an app 31110 might include an EMR app 31150, and settings 31130 might include an EMR app configuration 31160.

In addition, the wire cable 30010 may be adapted to enable the remote device 32000 to recharge an internal power source 32100 when the wire cable 30010 is coupled to an external power source 34000. An internal power source 32100 may include, for instance, a rechargeable battery, a non-rechargeable battery, a battery backup, an uninterrupted power supply ("UPS"), a solar-powered generator, a photovoltaic cell or array of cells, etc.

Figure 4:
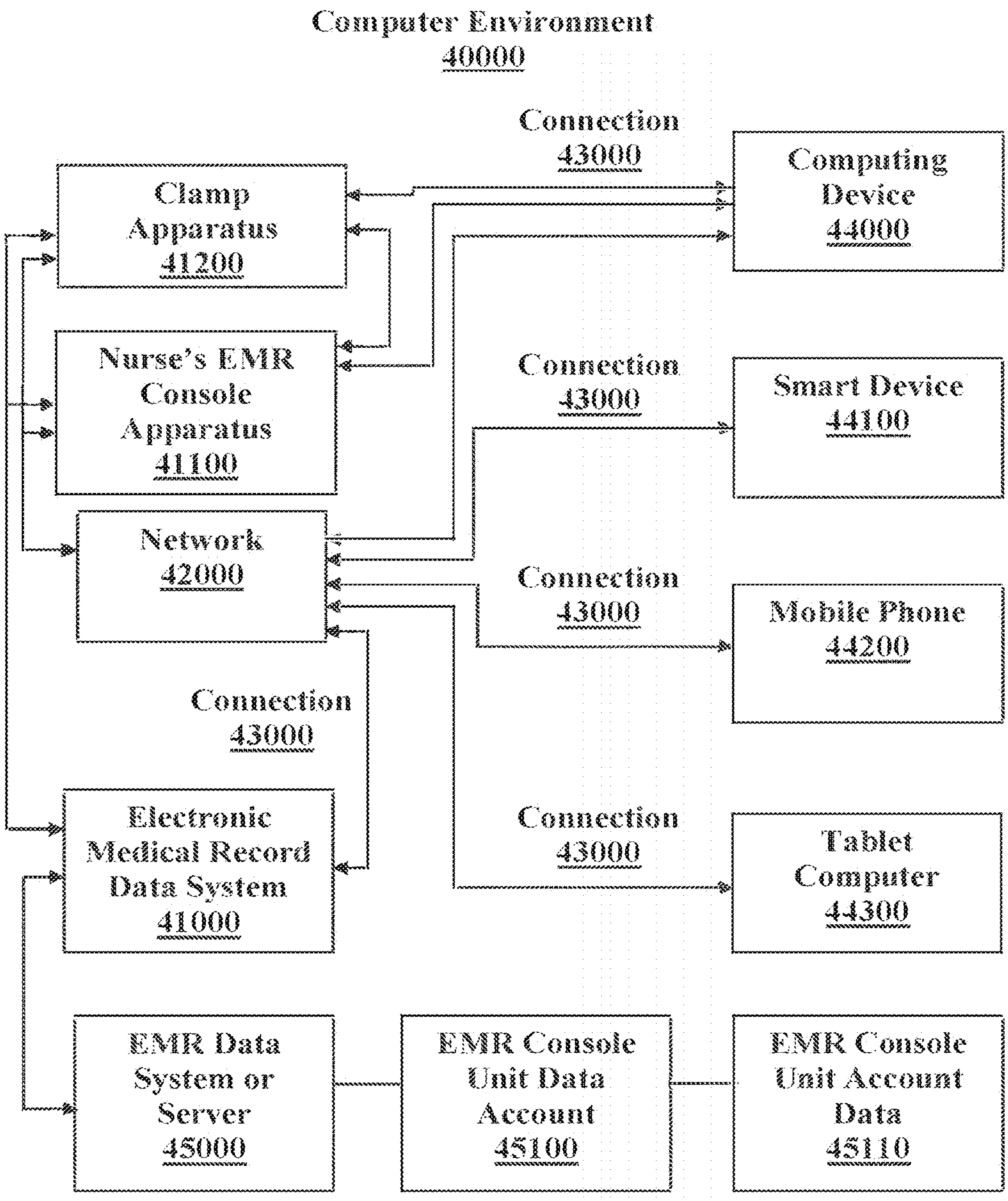
FIG. 4 shows a block diagram of an exemplary computer environment for use with the systems and methods in accordance with an embodiment of the present invention, and according to aspects of the invention.
Figure 5:
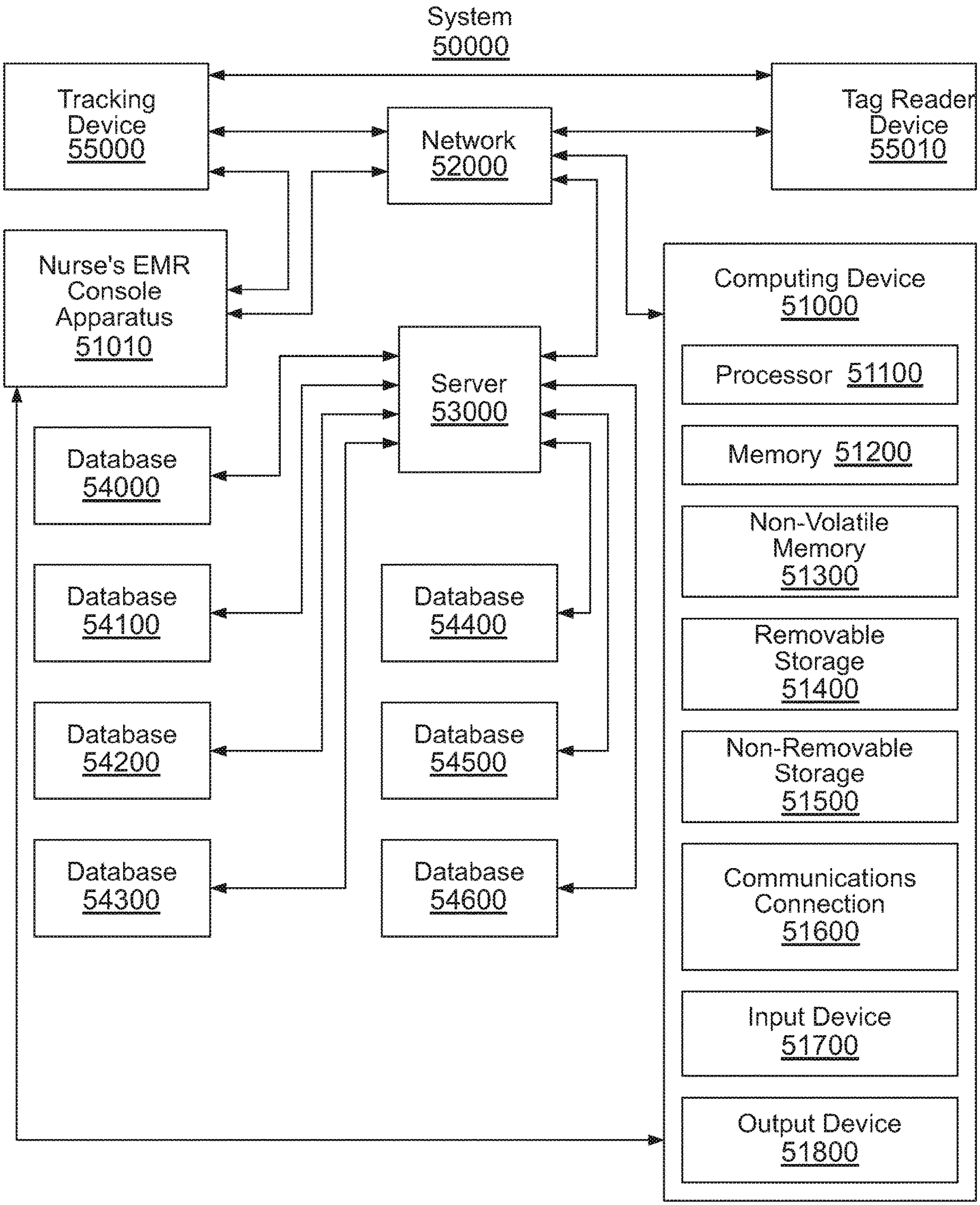
FIG. 5 shows a block diagram of an exemplary system, and an exemplary set of databases for use within the exemplary computer environment, for use with systems and methods in accordance with an exemplary embodiment of the present invention, according to aspects of the invention.

Referring to FIGS. 4-5 below, exemplary embodiments of the present invention may include a system for interactive communication adapted for professional use in a hospital or other medical care environment by a participant, wherein the system comprises an EMR platform, and possibly an integrated EMR server platform, a networked EMR data server, and/or a third-party EMR server, platform, or service, and an apparatus adapted to interact with EMR platform and the EMR platform. The system further may comprise a separate device software application running on at least one separate computing device, wherein the separate device software application may be adapted to enable the separate computing device: to interact with the clamp apparatus 11000, EMR console 12000, and/or wireless transceiver apparatus 14000; to modify settings of the clamp apparatus 11000, EMR console 12000, and/or wireless transceiver apparatus 14000; to upload data and files to the clamp apparatus 11000, EMR console 12000, and/or wireless transceiver apparatus 14000; to download data and files from the clamp apparatus 11000, EMR console 12000, and/or wireless transceiver apparatus 14000; and to control features and functions of the clamp apparatus 11000, EMR console 12000, and/or wireless transceiver apparatus 14000.

The system further may comprise a remote computing network and a user account platform accessible via the remote computing network and adapted to communicate with and transfer electronic data to and from the EMR platform, the clamp apparatus, and the EMR console, adapted to communicate with and transfer electronic data to and from the separate computing device, and adapted to enable the clamp apparatus and/or the EMR console to communicate with and transfer electronic data to and from the separate computing device via the remote computing network. The system further may comprise a user account accessible via the user account platform that enables the power user to log into the user account to remotely manage, view, and share data and settings of the EMR console and the user's account on the EMR platform that are available in the user account via the remote computing network, either because the data and settings have been uploaded to the user account platform, or because the EMR console is in communication with the user account platform via the remote computing network while the power user is accessing the user account platform and logged into the user account. In some embodiments, the user account may be adapted to enable the power user to set alert options to have an alert generated and sent to the separate computing device if an interaction with the first participant happens and notification of the interaction has been communicated from an EMR console and the user account platform via the remote computing network. The user account further may be adapted to enable the power user to email, upload, download, otherwise electronically share, or any combination thereof, an EMR app, an EMR app configuration, or other data file, such as an interaction file of a record of an interaction of the first participant with the EMR console.

The system further may comprise an EMR app configuration data file stored on the remote computing network and downloadable from the user account platform to the separate computing device and to the EMR console, wherein the EMR configuration data file is adapted to enable the EMR console to add further features, perform additional functions, or both. An EMR configuration may include, for instance, details relevant to a performance or experience, such as a map (e.g., an ariel map, a road map, a topography map, a resources map, a route map, a perspective view map, a plan view map, a point-of-view map, etc.), a user interface ("UI") utility (e.g., switch points of view, reveal details, switch profiles, synchronization of accounts, etc.), a terrain (e.g., a hospital, a parking lot, a city, a town, etc.), a tool (e.g., a clamp cutter, a vehicle, a unit or type of medication, a unit or type of nutrition, etc.), a capability (e.g., applying, attaching, cutting, removing, etc.), an avatar (e.g., a nurse, a doctor, a patient, a newborn baby, an expectant mother, a post-delivery mother, a father, etc.), and a communication utility (e.g., an electronic medical records (EMR) interface, a social media connection, a message feed, etc.).

A user of the EMR platform may include, for instance, a nurse, a doctor, a patient, a consumer, a producer, a performer, a business, a developer, an administrator, etc., or a combination thereof. A user may create and/or distribute a configuration, or both, by using the platform for user-based creation and/or distribution of configurations. Each configuration may be software code in a configuration file that includes, for instance, one or more of a settings file, a configuration file, a profile file, an applet file, an application file, a plug-in file, an application programming interface ("API") file, an executable file, a library file, an image file, a video file, a text file, a database file, a metadata file, and a message file. A user may develop the software code for the configuration file using, for instance, programming in coding languages, such as JavaScript and HTML, including open-source code, or object-oriented code assembly. The software code would be adapted to be compatible with and executable by the software of a console (e.g., an iPhone smartphone) on which a compatible video may be displayed, with which or within which the configuration would be used.

Referring to FIG. 4, FIG. 4 shows a diagram of an exemplary computer environment for use with the systems and methods in accordance with an embodiment of the present invention, and according to aspects of the invention. FIG. 4 illustrates a schematic diagram of an exemplary computer environment 40000 for creating, receiving, sending, exchanging, updating, and processing data in accordance with an embodiment of the present invention.

In the depicted embodiment, computer environment 40000 includes, inter alia, EMR data system 41000, network 42000, connections 43000, and at least one computing device 44000, such as computing devices smart device 44100, mobile smartphone 44200, and tablet computer 44300. The data system 41000 may comprise an EMR console apparatus 41100 and claim apparatus 41200 for use in EMR platform, possibly with its own integrated media server and/or service, or connectable to a third-party EMR server and/or system 45000 for data and media content, such as for a hospital. The network 42000 may connect to an EMR data system 45000 that accesses an EMR console data account 45100 for the transfer of EMR console account data 45110. Computing devices 44100, 44200, and 44300 are connected to network 42000 via connections 43000, which may be any form of network connection known in the art or yet to be invented. Connections 43000 may include, but are not limited to, telephone lines (e.g., xDSL, TI, leased lines, etc.), cable lines, power lines, wireless transmissions, and the like. Computing devices 44100, 44200, and 44300 include any equipment necessary (e.g., switches, modems, routers, etc.), as is known in the art, to facilitate such communication with the network 42000. EMR data system 41000 also may be connected to network 42000 using one of the aforementioned methods or other such methods known in the art.

Using inventive apparatus, system, and methods, such as depicted in FIGS. 1-5, a user may access the computer environment 40000 via a computing device connected to network 42000 such as computing device 44000. Computing device 44000 may include an auxiliary processing unit ("APU") 33010, which may function as an intermediate computing device for use between EMR console apparatus 41100, clamp apparatus 41200, and EMR data system 41000. Such a computing device may be, for instance, a beacon, a location reader, a perimeter port, a data bridge, a sub-router, a data communication range extender, or a combination thereof, possibly as a commercial embodiment of APU 33010, or alternatively an individual's personal computer, an Internet café computer, a matrix of readers, a computerized portable electronic device (e.g., a laptop, a tablet, a personal data assistant, a cell phone, etc.), or the like. For example, a smartphone 44200 may or a tablet computer 44300 act as an APU 33010 serving as a communications bridge to a clamp apparatus 41200 by providing a "hotspot" to allow the clamp apparatus 41200 to use the network connectivity of the smartphone 44200 to connect to a server 42000.

Using the apparatus, system, and methods depicted in FIGS. 1-5, such user access may include a download of data to, and/or an upload of data (e.g., an electronic form of information) from, a computing device 44100, 44200, and 44300 via network 42000 to EMR data system 41000 (e.g., server, mainframe, computer, etc.), wherein EMR data system 41000 is typically provided and/or managed by the hospital entity implementing the process or its affiliate, subcontractor, or the like.

Although the systems and methods disclosed herein have focused on embodiments in which user access initiates the process, one of skill in the art may easily appreciate that such systems and methods may be equally applied for other scenarios in which the process is not initiated by the user, and in which the process proceeds under the control of the EMR data system 41000, which may initiate the EMR process in accordance with settings or parameters, such as upon the commencement of an event, such as a tamper alert, a removal or perimeter alarm, a low-battery alert, etc. For example, EMR data system 41000 may push content to a user upon the user arriving at or connecting from a specified location, in which the content is associated with the specified location, such as the crib of a specific newborn baby, or with a topic or a subject matter relevant to the specified location, such as medication for the specific newborn baby.

Referring to FIG. 5, FIG. 5 shows a block diagram of an exemplary data system for use with systems and methods in accordance with an exemplary embodiment of the present invention, according to aspects of the invention. In addition, FIG. 5 shows an exemplary set of databases, libraries, or data tables for use with the exemplary computer environment, in accordance with the exemplary embodiment of the present invention, according to aspects of the invention. FIG. 5 depicted herein represents an exemplary computing system environment for allowing a user of system 50000 to perform the methods described with respect to FIGS. 1-4.

The depicted computing system environment is only one example of a suitable computing environment and is not intended to suggest any limitation as to the scope of use or functionality. Apart from a customized EMR apparatus 51010, and a novel clamp apparatus as a tracking device 55000, numerous other general-purpose or special-purpose computing devices, system environments or configurations may be used, within appropriate application-specific customizations. Examples of well-known computing systems, environments, and/or configurations that may be suitable for use include, but are not limited to, personal computers ("PCs"), server computers, handheld or laptop devices, multi-processor systems, microprocessor-based systems, network PCs, minicomputers, mainframe computers, cell phones, smartphones, tablets, embedded systems, distributed computing environments, cloud-based systems, that include any of the above systems or devices, and the like.

Computer-executable instructions such as program modules executed by a computer may be used. Generally, program modules include routines, programs, objects, components, data structures, etc., that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

FIG. 5 depicts an exemplary system 50000 for implementing embodiments of the present invention. This exemplary system includes, inter alia, one or more computing devices 51000, a network 52000, and at least one server 53000, which interface to each other via network 52000, and access at least one database 54000, to track at least one clamp apparatus as a tracking device 55000, such as using at least one reader device 55010, such as in a matrix of reader devices 55010 placed throughout a hospital. A computing device 51000 may include a console apparatus 12000, an EMR console 32000, an EMR apparatus 51010, an auxiliary processing unit 33010 of an apparatus 51010, and/or an EMR apparatus 51010 having an auxiliary processing unit 33010 connected to the EMR console 32000, such as described in the embodiments of FIGS. 1-3. In its most basic configuration, computing device 51000 includes at least one processing unit, processor 51100, and at least one memory unit 51200. Depending on the exact configuration and type of the computing device, memory 51200 may be volatile (such as random-access memory ("RAM")), non-volatile (such as read-only memory ("ROM"), solid state drive ("SSD"), flash memory, etc.), or some combination of the two. A basic configuration is illustrated in FIG. 5 by non-volatile memory 51300. In addition to that described herein, computing devices 51000 can be any web-enabled handheld device (e.g., cell phone, smart phone, or the like) or personal computer including those operating via Android, Apple, and/or Windows mobile or non-mobile operating systems.

Computing device 51000 may have additional features and/or functionality. For example, computing device 51000 may include additional storage (removable and/or non-removable) including, but not limited to, magnetic or optical disks or tape, thumb drives, and external hard drives as applicable. Such additional storage is illustrated in FIG. 5 by removable storage 51400 and non-removable storage 51500.

Computing device 51000 typically includes or is provided with a variety of computer-readable media. Computer-readable media can be any available media that can be accessed by computing device 51000 and includes both volatile and non-volatile media, removable and non-removable media. By way of example, and not limitation, computer-readable media may comprise computer storage media and communication media.

Computer storage media includes volatile and non-volatile, removable and non-removable media implemented in any method or technology for storage of information such as computer-readable instructions, data structures, program modules or other data. Memory 51200, removable storage 51400, and non-removable storage 51500 are all examples of computer storage media. Computer storage media includes, but is not limited to, RAM, ROM, electrically erasable programmable read-only memory ("EEPROM"), flash memory or other memory technology, CD-ROM, digital versatile disks ("DVD") or other optical storage, magnetic cassettes, magnetic tape, magnetic disk storage or other magnetic storage devices, or any other medium that can be used to store the desired information, and that can be accessed by computing device 51000. Any such computer storage media may be part of computing device 51000 as applicable.

Computing device 51000 may also contain a communications connection 51600 that allows the device to communicate with other devices. Such communications connection 51600 is an example of communication media. Communication media typically embodies computer-readable instructions, data structures, program modules and/or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency ("RF"), infrared and other wireless media. The term computer-readable media as used herein includes both storage media and communication media.

Computing device 51000 may also have input device(s) 51700 such as keyboard, mouse, pen, camera, light sensor, motion sensor, infrared ("IR") sensor, accelerometer, inertia motion unit ("IMU"), voice input device, touch input device, etc. Output device(s) 51800 such as a display, speakers, LED light, printer, etc. may also be included. Some input devices 51700 may be considered output devices 51800 for other components, such as a camera providing a video feed, or a sensor providing data on the activity that is sensed. All these devices are generally known to the relevant persons of skill in the art and therefore need not be discussed in any detail herein except as provided.

Notably, computing device 51000 may be one of a plurality of computing devices 51000 inter-connected by a network 52000. As may be appreciated, network 52000 may be any appropriate network and each computing device 51000 may be connected thereto by way of connection 51600 in any appropriate manner. In some instances, each computing device 51000 may communicate with only the server 53000, while in other instances, computing device 51000 may communicate with one or more of the other computing devices 51000 in network 52000 in any appropriate manner. For example, network 52000 may be a wired network, wireless network, or a combination thereof within an organization or home, or the like, and may include a direct or indirect coupling to an external network such as the Internet or the like. Likewise, the network 52000 may be such an external network. Network 5200 may allow for a number of computing devices 51000 with capabilities utilizing internet of things (IoT) to establish secure connections between physical products online connected tag readers and the like. The IoT environment may be particularly useful for smart tags, which unlike simple RFID tags, are sensor-enabled tags that actively generate and send metrics and other data in real-time. This expansion of capabilities makes connected devices truly "smart." For example, the tags may further monitor ambient or body temperature, $O_2$ saturation, pulse rate, respiratory, and the like or some combination thereof.

Computing device 51000 may connect to a server 53000 via such an internal or external network. Server 53000 may serve, for instance, as an EMR platform, a media server, service, or platform, or both. Although FIG. 5 depicts computing device 51000 located in close proximity to server 53000, this depiction is not intended to define any geographic boundaries. For example, when network 52000 is the Internet, computing device can have any accessible physical location. For example, the computing device may be a tablet, cell phone, smartphone, personal computer, or the like located at any user's office, home, or other venue, etc. Or computing device could be located proximate to server 53000 without departing from the scope hereof. Also, although FIG. 5 depicts computing devices 51000 coupled to server 53000 via network 52000, computing devices may be coupled to server 53000 via any other compatible networks including, without limitation, an intranet, local area network, or the like.

The system may use a standard client-server technology architecture, which allows users of the system to access information stored in the relational databases via custom user interfaces. An application may be hosted on a server such as server 53000, which may be accessible via the Internet, using a publicly addressable Uniform Resource Locator ("URL"). For example, users can access the system using any web-enabled device equipped with a web browser. Communication between software component and sub-systems are achieved by a combination of direct function calls, publish and subscribe mechanisms, stored procedures, and direct SQL queries.

In some embodiments, for instance, server 53000 may be provided as a service, such as via Amazon Web Services ("AWS"), or as a dedicated stand-alone service, such as an Edge R200 server manufactured by Dell, Inc., however, alternate servers may be substituted without departing from the scope hereof. System 50000 and/or server 53000 utilize a PHP scripting language to implement the processes described in detail herein. However, alternate scripting languages may be utilized without departing from the scope hereof.

An exemplary embodiment of the present invention may utilize, for instance, a Linux variant messaging subsystem. However, alternate messaging subsystems may be substituted including, without limitation, a Windows Communication Foundation ("WCF") messaging subsystem of a Microsoft Windows operating system utilizing a .NET Framework 3.0 programming interface.

Also, in the depicted embodiment, computing device 51000 may interact with server 53000 via a Transmission Control Protocol/Internet Protocol ("TCP/IP") communications protocol; however, other communication protocols may be substituted.

Computing devices 51000 may be equipped with one or more Web browsers to allow them to interact with server 53000 via a HyperText Transfer Protocol ("HTTP") and/or a secure version (e.g., "https") of a related Uniform Resource Locator ("URL"). HTTP functions as a request-response protocol in client-server computing. For example, a web browser operating on computing device 51000 may execute a client application that allows it to interact with applications executed by server 53000. The client application submits HTTP request messages to the server. Server 53000, which provides resources such as HTML files and other content, or performs other functions on behalf of the client application, returns a response message to the client application upon request. The response typically contains completion status information about the request as well as the requested content. However, alternate methods of computing device/server communications may be substituted without departing from the scope hereof.

In the exemplary system 50000, server 53000 includes one or more databases 54000 as depicted in FIG. 5, which may include a plurality of libraries or database tables including, without limitation, Templates, Users, Events, Memories, Moments, Maps, Utilities, User Uploads, Admin Info, Transactions, Status, Tracking, and/or Location database tables, e.g., 54100 through 54600. As may be appreciated, database(s) 54000 may be any appropriate database capable of storing data and it may be included within or connected to server 53000 or any plurality of servers similar to 53000 in any appropriate manner.

In the exemplary embodiment of the present invention depicted in FIG. 5, database(s) 54000 may be structured query language ("SQL") database(s) with a relational database management system, namely, MySQL as is commonly known and used in the art. Database(s) 54000 may be resident within server 53000. However, other databases may be substituted without departing from the scope of the present invention including, but not limited to, PostgreSQL, Microsoft® SQL Server 2008 MySQL, Microsoft® Access®, and Oracle databases, and such databases may be internal or external to server 53000.

The various techniques described herein may be implemented in connection with hardware or software or, as appropriate, with a combination of both. Thus, the methods and apparatus of the presently disclosed subject matter, or certain aspects or portions thereof, may take the form of program code (i.e., instructions, scripts, and the like) embodied in tangible media, such as floppy diskettes, CD-ROMs, hard drives, or any other machine-readable storage medium wherein, when the program code is loaded into and executed by a machine, such as a computer, the machine becomes an apparatus for practicing the presently disclosed subject matter.

In the case of program code execution on programmable computers, the interface unit generally includes a processor, a storage medium readable by the processor (including volatile and non-volatile memory and/or storage elements), at least one input device, and at least one output device. One or more programs may implement or utilize the processes described in connection with the presently disclosed subject matter (e.g., through the use of an application programming interface ("API"), reusable controls, or the like). Such programs may be implemented in a high-level procedural or object-oriented programming language to communicate with a computer system. However, the program(s) can be implemented in assembly or machine language, if desired. In any case, the language may be a compiled or interpreted language, and combined with hardware implementations.

Although exemplary embodiments may refer to utilizing aspects of the presently disclosed subject matter in the context of one or more stand-alone computer systems, the subject matter is not so limited, but rather may be implemented in connection with any computing environment, such as a system 50000 or a distributed computing environment 40000. Still further, aspects of the presently disclosed subject matter may be implemented in or across a plurality of processing chips or devices, and storage similarly may be created across a plurality of devices in system 50000. Such devices might include personal computers, network servers, and handheld devices (e.g., cell phones, tablets, smartphones, etc.), for example.

In the exemplary embodiment, server 53000 and its associated databases are programmed to execute a plurality of processes including those shown in FIGS. 1-4 as discussed in greater detail herein.

Methods in accordance with aspects of the invention include, for instance, a method for interactive communication adapted for tracking electronic medical records, including those of a clamp apparatus, wherein the method comprises providing an apparatus, such as clamp apparatus 11000 and/or console apparatus 12000, adapted for interaction with a participant, such as a nurse participant 12011; configuring the apparatus to interact with the participant; enabling the apparatus to interact with the participant; and capturing electronically in the apparatus status data, status data, or both, of an interaction of the apparatus with the participant. Further embodiments of the method may include performing the actions associated the functionalities set forth in FIGS. 1-5, such as using clamp apparatus 11000 with the EMR console apparatus 12000, within the computing environment 40000, and within the system 10000 and/or 50000.

Figure 6:
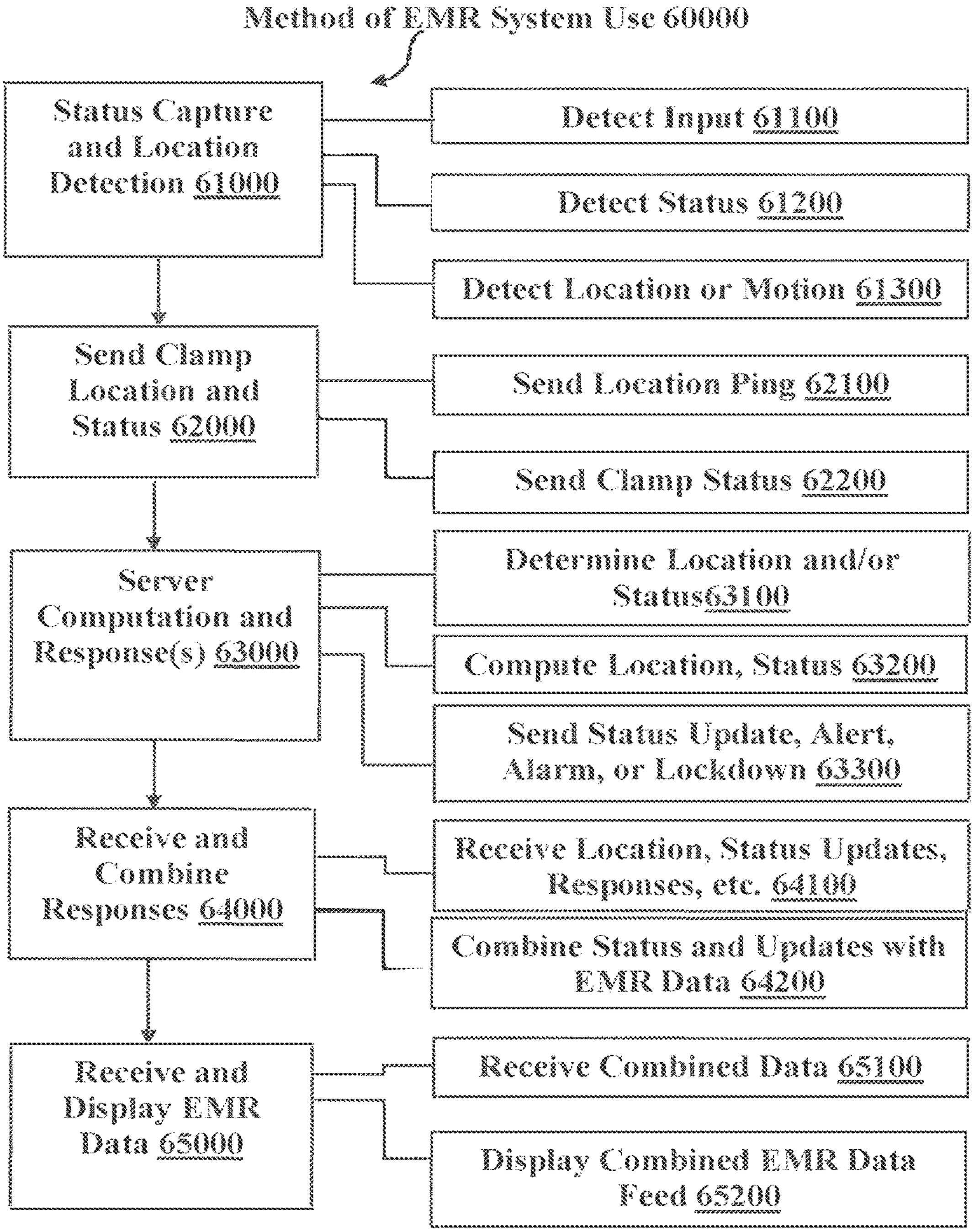
FIG. 6 shows a block diagram of an exemplary embodiment of a method of use of an exemplary system, according to aspects of the invention.

Referring to FIG. 6, FIG. 6 shows a block diagram of an exemplary embodiment of a method 60000 of use of an exemplary EMR system, according to aspects of the invention. In the method 60000 as depicted in FIG. 6, the AR system may perform a step 61000 of status capture and location detection at the apparatus. The status capture and location detection step 61000 may include, for instance, detecting 61100 an input, such as a switch or button press to activate the apparatus; detecting 61200 a status of the apparatus captured or generated by a console apparatus, such as in which the status is detected during an attachment of a clamp apparatus to an umbilical cord of a newborn baby; and detecting location or motion 61300, in some embodiments in real time (both in tracking as well as locating), such as to generate positioning data and/or to indicate a location within a hospital that the clamp apparatus is located or is being moved or handled by a user. The EMR system may perform a step 62000 at the clamp apparatus of transmission of location ping signal output, which may be received at a console apparatus or a wireless transceiver apparatus, and sent to a server, such as via an auxiliary processor unit. This transmission step 62000 may include sending 62100 the location ping signal receipt data from the signal reader to the server, possibly via the auxiliary processor unit, for combination with an EMR file for the newborn; and sending 62200 the clamp status data feed from the clamp apparatus, via a reader or auxiliary processor unit, to the server; for location calculations and determinations of the appropriate EMR response. The EMR system may perform a step 63000 at the server of server computation and response(s) to the transmission step 62000. This computation and response step 63000 may include determining 63100 a location (e.g., in a nursery, in mother's room, etc.) and/or a status (e.g., operational, activated, low-battery, etc.) of the clamp apparatus within the hospital; computing 63200 a corresponding location interpretation and response (e.g., the clamp apparatus is within authorized location, so no action is needed; the clamp apparatus is being moved toward an exit from an authorized location, so an alert and a lockdown are needed; the clamp apparatus is not within authorized location, so an alarm for possible abduction is needed; etc.) and/or status interpretation and response(s) (e.g., operational status, so no action needed; low battery status, so replacement or recharging is needed; no longer operational or deactivated, so a tamper alert or removal alarm is needed; etc.), and sending 63300 the response(s) to the console apparatus. The EMR system may perform a step 64000 at the console apparatus of receipt and combination of responses from the server. The receipt and combination of responses step 64000 may include receiving 64100 the location and status updates and responses, and combining 64200 the location updates, status updates, and associated responses in the corresponding EMR file for the newborn baby. The EMR system may perform the step 65000 at the console apparatus of receipt and display of the updated and combined data. The receipt and display EMR data step 65000 may include receiving 65100 the combined data feed comprising the clamp apparatus' determined location, the computed location interpretation, the computed location response, the determined status, the computed status interpretation, the computed status response, and displaying 65200 the combined data feed on the display of the console apparatus.

Figure 7:
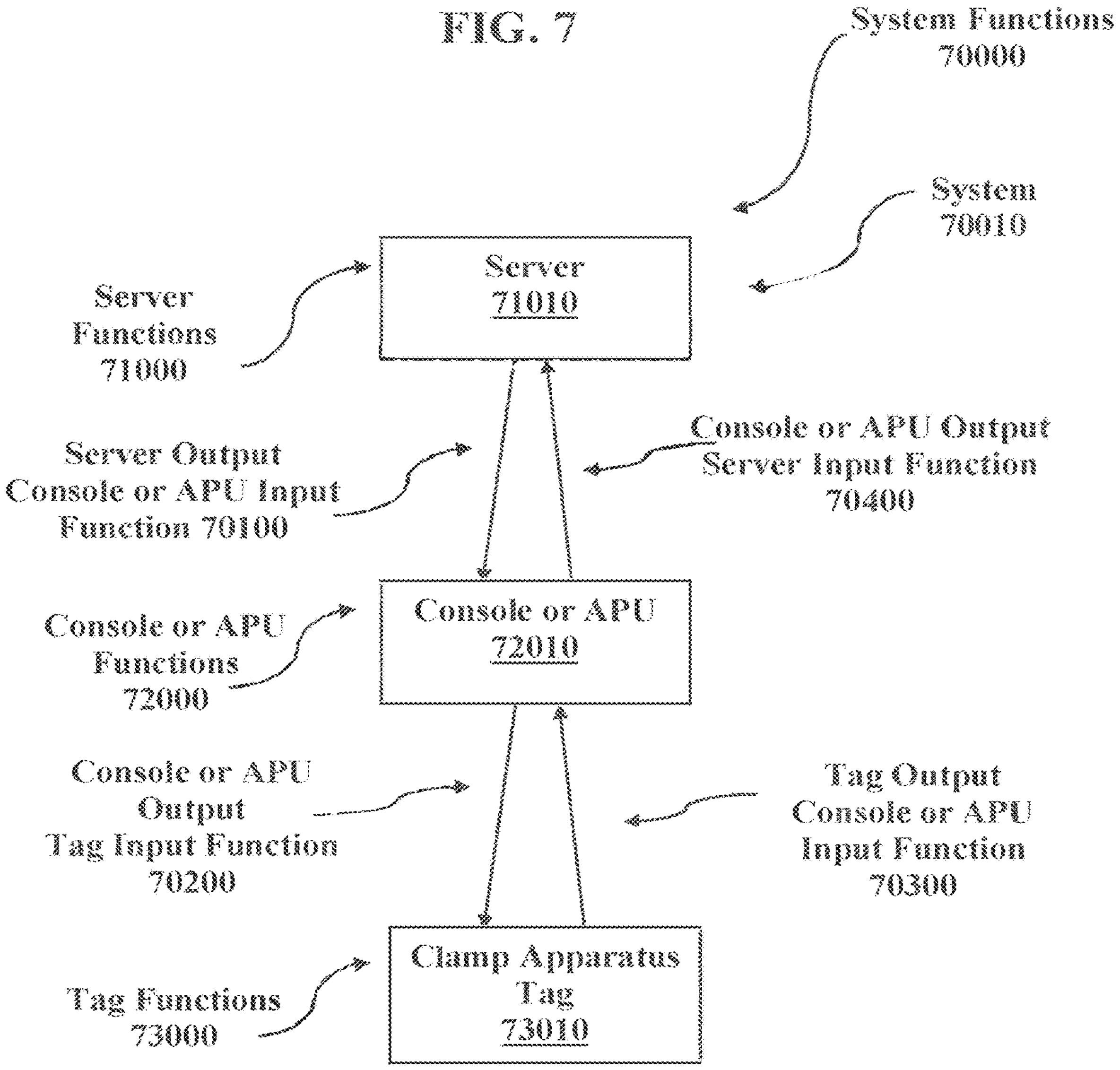
FIG. 7 shows a conceptual block diagram of an exemplary system functions operation flow within systems and methods in accordance with an exemplary embodiment of the present invention, according to aspects of the invention.

Referring to FIG. 7, FIG. 7 shows a conceptual block diagram of an exemplary system functions 70000 operation flow within a system 70010 and with methods in accordance with an exemplary embodiment of the present invention, according to aspects of the invention. The embodiment of FIG. 7 depicts an exemplary embodiment of the system and is not limiting of the invention overall. The depicted system functions 70000 conceptually may be divided into the server functions 71000 of server 71010, console or auxiliary processing unit (APU) functions 72000 of console or APU 72010, and clamp apparatus tag functions 73000 of a wireless tag 73010 of a clamp apparatus. The system functions 70000 conceptually may be divided into the server output, console or APU input functions 70100; the console or APU output, tag input functions 70200; the tag output, console or APU input functions 70300; and the console or APU output, server input functions 70400. In this depicted embodiment, the APU 72010 might be a wireless transceiver apparatus 13000, such as a tag reader in a matrix of tag readers distributed through a hospital, that communicates with a server 71010, whereas console 72010 that may be a smartphone running an app functioning as a nurse's console apparatus 12000 that communicates with the server 71010.

At a high conceptual level, a data flow may be represented by the server output, console or APU input functions 70100; the console or APU output, tag input functions 70200; the tag output, console or APU input functions 70300; and the console or APU output, server input functions 70400. For example, the server 71010 may connect to the console 72010 using the server output, console input functions 70100 to push patient-based EMR data to the console 72010. The console 72010 may then communicate some of the patient-based EMR data to the tag 73010 to initiate activation and status capture by the tag 73010, using the console output, tag input functions 70200. The tag 73010 may send location data and status data back to the console 72010, using tag output, console input functions 70300, for the location data and status data to be combined with EMR content received from the server 71010. The console 72010 may transfer some location data and/or status data to the server 71010 using the console output, server input functions 70400. For example, the tag output, console input functions 70300 might comprise the tag 73010 generating low-battery status data that are transferred to the console 72010. An APU 72010 might receive tag location ping signals as a tag output, APU input function 70300, and send the location ping data to the server 71010 as an APU output, server input function 70400, for the server 71010 to generate location data for the tag. As a server function 71000, the server 71010 may use the location data and status data to generate an appropriate interpretation and response to the location data and status data, including timing of the location data or status data relative to the events in the EMR data (e.g., a scheduled discharge of a newborn from the hospital), and sending the response to the console 72010. As a console function 72000, the console 72010 may combine the location interpretation, location response, status interpretation, and status response with the EMR data to create and display an updated EMR data feed, and possibly sending an updated data feed to the tag 73010, such as if the tag 73010 is to be deactivated by an authorized user. If the tag 73010 is updated, a tag function 73000 includes storing the updated data. If the console 72010 includes a display, the console functions 72000 may include displaying the EMR data on the display of the console for viewing by a user.

Figure 8:
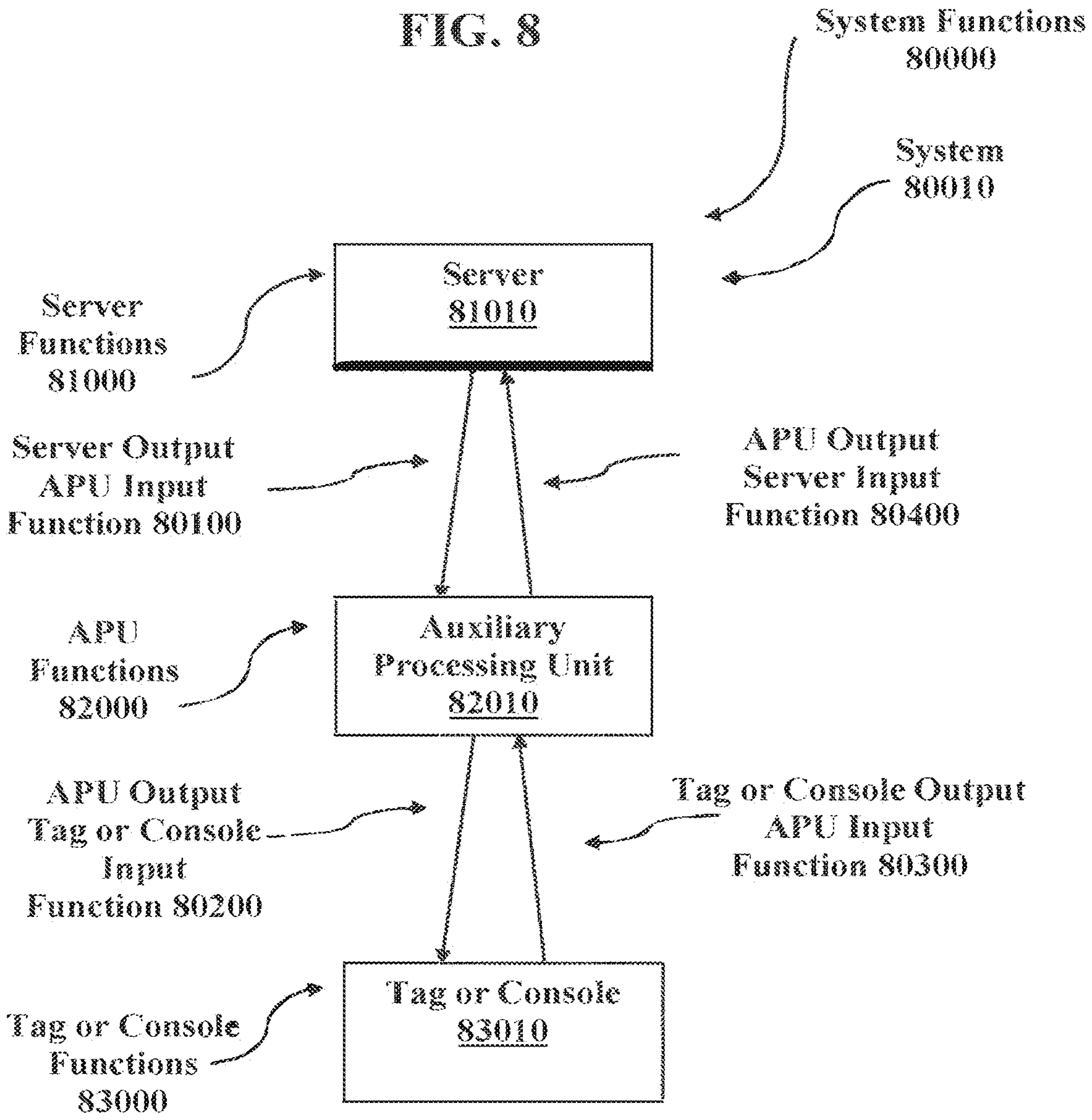
FIG. 8 shows a conceptual block diagram of an exemplary apparatus operation, as an apparatus within a system used pursuant to a method in accordance with an exemplary embodiment of the present invention, according to aspects of the invention.

Referring to FIG. 8, FIG. 8 shows a conceptual block diagram of an exemplary system functions 80000 operation flow within a system 80010 and with methods in accordance with an exemplary embodiment of the present invention, according to aspects of the invention. The embodiment of FIG. 8 depicts an exemplary embodiment of the system and is not limiting of the invention overall. The depicted system functions 80000 conceptually may be divided into the server functions 81000 of server 81010, auxiliary processing unit functions 82000 of auxiliary processing unit ("APU") 82010, and tag or console functions 83000 of a tag or console 83010. The system functions 80000 conceptually may be divided into the server output, APU input functions 80100; the APU output, console or tag input functions 80200; the tag or console output, APU input functions 80300; and the APU output, server input functions 80400. In this depicted embodiment, the APU 82010 might be a separate computing device, such as a tablet, laptop, or desktop computer; or a wireless transceiver apparatus 13000, such as in a matrix of wireless routers, wireless range extenders, and/or wireless tag readers distributed throughout a hospital; or an intermediate buffering server; that communicates with a wireless tag 83010 of a clamp apparatus 11000, and/or with a console 83010 that may be a nurse's console apparatus 12010 that communicates with the server 81010 via, at least in part, the APU 82010.

At a high conceptual level, a data flow may be represented by the server output, APU input functions 80100; the APU output, tag or console input functions 80200; the tag or console output, APU input functions 80300; and the APU output, server input functions 80400. For example, the server 81010 may connect to the APU 82010 using the server output, APU input functions 80100 to push patient-based EMR data to the APU 82010. The APU 82010 may then communicate the patient-based EMR data to the console 83010 to update the EMR data displayed by the console 83010, using the APU output, console input functions 80200. The console 83010 may send clamp apparatus status data back to the APU 82010, using console output, APU input functions 80300, for the status data to be forwarded by the APU 82010 to the server 81010 and combined with other EMR data, once received by the server 81010. The APU 82010 may transfer the data to the server 81010 using the APU output, server input functions 80400. For example, the console output, APU input functions 80300 might comprise the console 83010 generating tag activation status data that are transferred to the APU 82010. The tag 83010 might generate location ping signal data and status data that the tag 83010 may send to the APU 82010 as a tag output, APU input function 80300. The APU 82010 might transfer the location ping data and status data to the server 81010 as an APU output, server input function 80400. As a server function 81000, the server 81010 may use the location data and/or status data to generate an appropriate interpretation and response to the location data and the status data, relative to the other EMR data and timing of the location data and status data relative to the other EMR data, and the server 81010 may send the interpretation and response data to APU 82010 to be forwarded to and displayed on the console 83010. As a potential APU function 82000, the APU 82010 may combine the interpretation and response data with the EMR data to create an updated EMR data feed sent to the console 83010. As a console function 83000, the console 83010 may display the updated EMR data feed. If the APU 82010 includes a display as well, the APU functions 82000 may include displaying the update EMR data on the display of the APU also, such as for monitoring what a user is viewing on the console 83010. For example, an APU 82010 may comprise a tag reader and a tablet computer, in which the tablet computer displays an image of a hospital floorplan with blinking beacon dots indicating approximate locations of wireless tags detected on that hospital floor.

As presented differently, the tag or console functions 83000 may comprise the tag or console 83010 generating EMR data, such as status data or location data of a clamp apparatus, and sending the EMR data to the auxiliary processing unit 82010. The auxiliary processing unit functions 82000 may include the APU 82010 receiving the EMR data from the tag or console 83010 and communicating with the server 81010 to have the server 81010 perform the server functions 81000 comprising generating updated EMR data that include an appropriate interpretation of and response to the updated EMR data and timing of the updated EMR data relative to the other EMR data, and sending the interpretations and responses from the server 81010 to the APU 82010. The APU functions 82000 further include the APU 82010 forwarding the updated EMR data to the tag or console 83010, and possibly combining aspects of the EMR data with other EMR data or system data to create an APU-specific data feed (e.g., animation of floorplan image with beacon dots indicating tag locations in real time). The tag or console functions 83000 include the tag or console 83010 storing the updated EMR data, and possibly displaying the updated EMR data on the display(s) of the console 83010 for viewing by a user, such as a nurse.

Figure 9A:
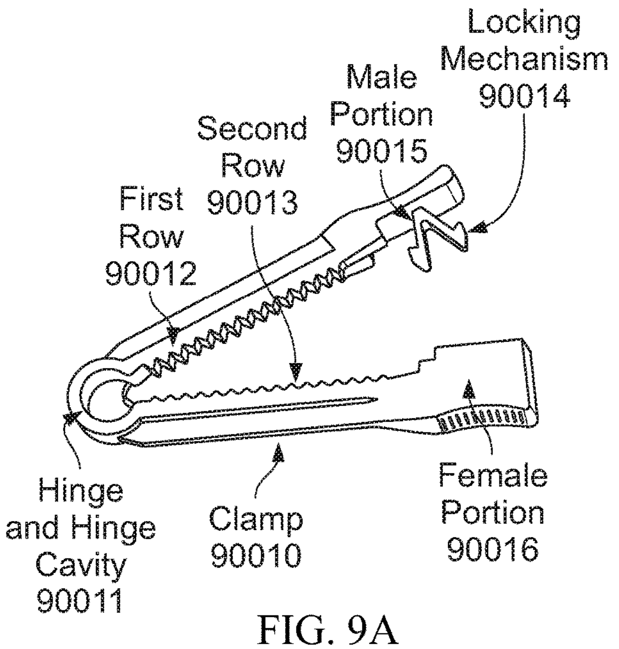
FIGS. 9A-9D shows various exemplary clamps, as an apparatus within a system used pursuant to a method in accordance with an exemplary embodiment of the present invention, according to aspects of the invention.

Referring to FIGS. 9A-9D, FIGS. 9A-9D shows various exemplary clamps 90000, as part of an umbilical cord clamp apparatus 11000 within a system 10000 used pursuant to a method in accordance with an exemplary embodiment of the present invention, according to aspects of the invention. As shown in FIG. 9A, clamp 90010 comprises a hinged clamp having a hinge and hinge cavity 90011, a first opposing row of teeth 90012, a second opposing row of teeth 90013, and a locking mechanism 90014, having a male portion 90015, and a female portion 90016. The hinge cavity is partially annular, forms an open partial ring when the clamp is open, and forms a closed ring when the clamp is closed. The hinge 90011 is adapted to align the first opposing row of teeth 90012 with the second opposing row of teeth, so that the first opposing row of teeth 90012 oppose and engage, but do not obstruct, the second opposing row of teeth 90013 when the clamp 90010 is closed. The hinge 90011 also is adapted to align the male portion 90015 and the female portion 90016 of the locking mechanism 90014, so that the male portion 90015 opposes, inserts into, and engages the female portion 90016 when the clamp 90010 is closed. The female portion 90016 comprises a cavity with an interior lip (not visible in the drawing) at the opening. The male portion 90015 resembles two flexible, opposing flanges, which may flex inward upon insertion into female portion 90016, and then flex outward within female portion 90016, to engage the interior lip. An umbilical cord of a newborn baby may be inserted between the first opposing row of teeth 90012 and the second opposing row of teeth 90013, and the clamp 90010 may closed to compress umbilical cord between rows 90012, 90013, thereby impeding further bleeding from the umbilical cord and serving as a tourniquet stopping circulation to the distal tip of the umbilical cord, causing the distal tip to dry out and eventually fall off.

Figure 9B:
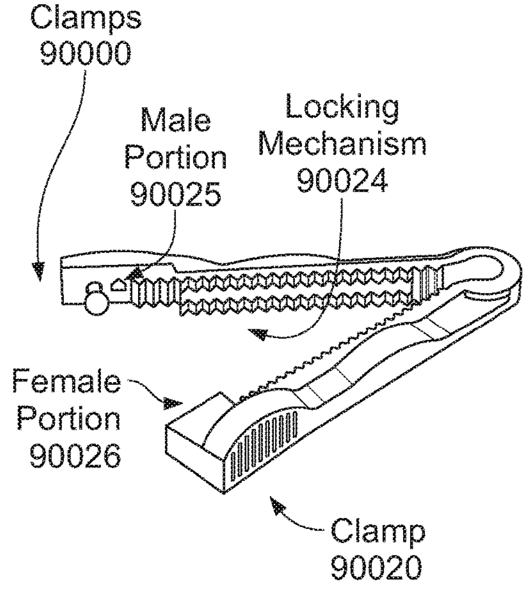

As shown in FIG. 9B, clamp 90020 comprises a variation of a hinged clamp, in which the locking mechanism 90024 includes a male portion 90025 comprising a tapered plug adapted to compress and deform when inserted into a female portion 90026, and decompress and engage an interior lip to lock the mechanism 90024.

Figure 9C:
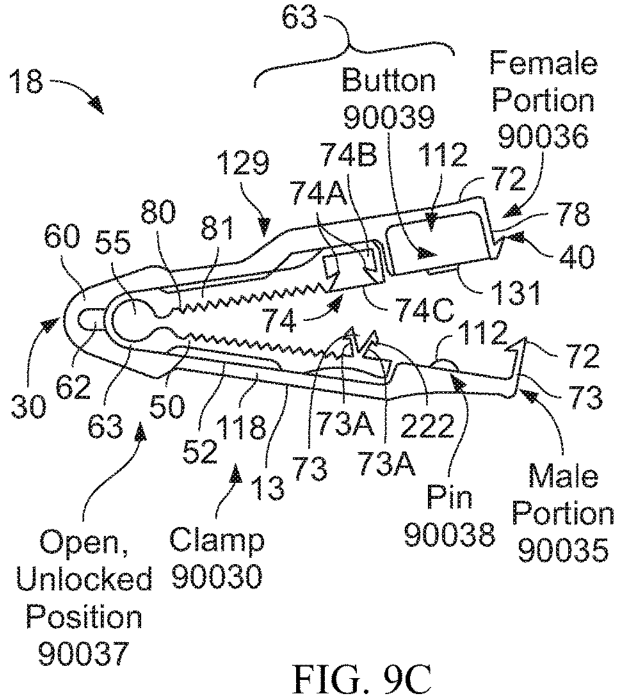

As shown in FIG. 9C, clamp 90030 comprises a variation of a hinged clamp, in which the locking mechanism 90034 includes a male portion 90035 comprising a flexible flanged lip adapted to flex outward when inserted into a female portion 90036, and flex inward and engage a lip of the female portion 90036 to lock the mechanism 90034. The locking mechanism 90034 may be reopened if the male portion 90035 is disengaged from the female portion 90036. The clamp 90030 is depicted in an open, unlocked position 90037, revealing a pin 90038 that may engage a button 90039. Button 90039 may comprise an electrical switch. Pin 90038 and button 90039 may comprise a tamper-evident switch that indicates possible tampering if the pin 90038 ceases to engage the button 90039 after the locking mechanism 90034 is closed (e.g., in a closed, locked position 90047), but then is reopened.

Figure 9D:
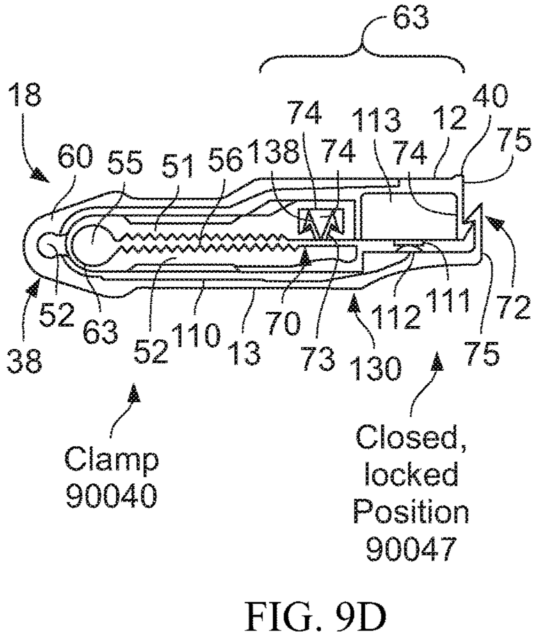

As shown in FIG. 9D, clamp 90040 comprises a variation of clamp 90030, depicted in a closed, locked position 90047. Although clamps 90010, 90020, 90030, and 90040 are variations of hinged clamps, some clamps may omit the hinge and replace the hinge with a second locking mechanism, such that a locking mechanism is on either side of the opposing rows of teeth.

Figure 10A:
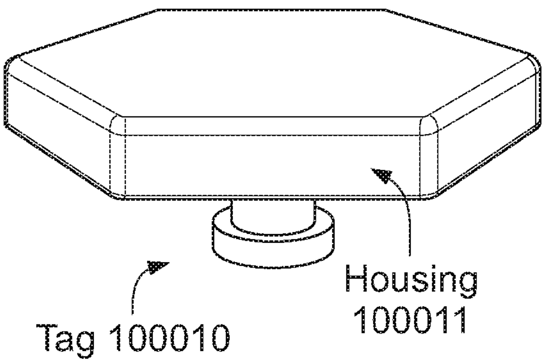
FIGS. 10A-10E shows depictions of wireless tags from different viewpoints that may be used in an exemplary apparatus within a system used pursuant to a method in accordance with an exemplary embodiment of the present invention, according to aspects of the invention.
Figure 10B:
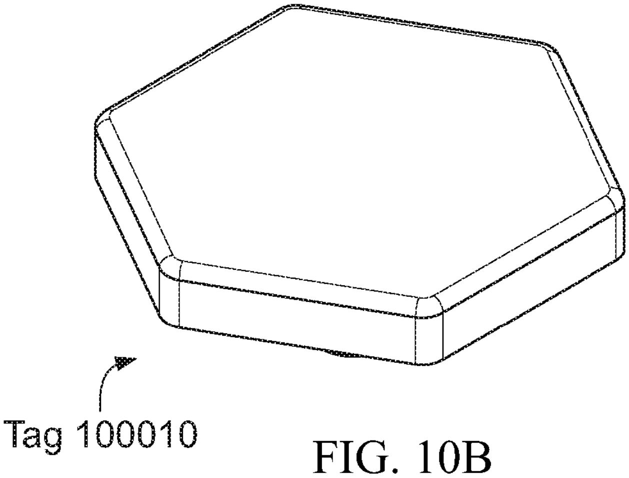
Figure 10C:
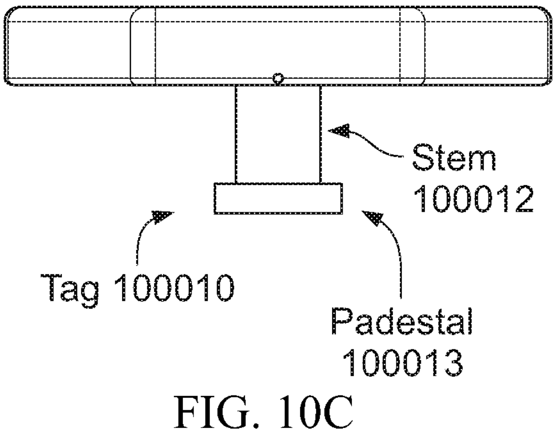
Figure 10D:
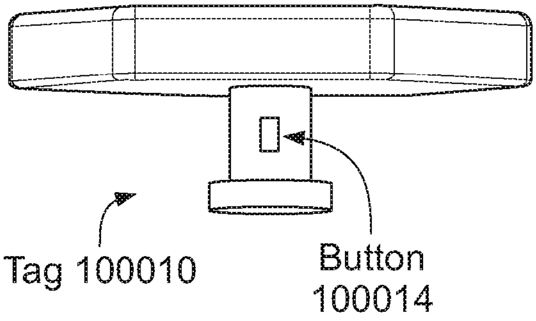
Figure 10E:
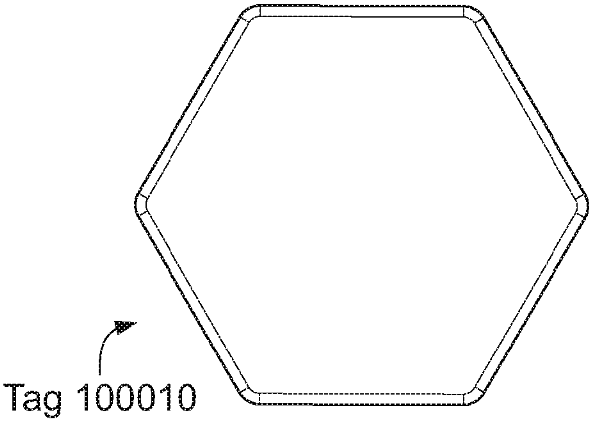

Referring to FIGS. 10A-10E, FIGS. 10A-10E shows depictions of wireless tags 100000 and specific tag 100010 from different viewpoints that may be used in an exemplary apparatus within a system used pursuant to a method in accordance with an exemplary embodiment of the present invention, according to aspects of the invention. The embodiment of FIGS. 10A-10E shows an exemplary proposed commercial embodiment of the system and is not limiting of the invention overall. FIG. 10A depicts a top perspective side view of tag 100010; FIG. 10B depicts a top perspective plan view of tag 100010; FIG. 10C depicts a side elevation view of tag 100010; FIG. 10D depicts a bottom perspective side view of tag 100010; and FIG. 10E depicts a top plan view of tag 100010. Tag 100010 includes a hexagonal housing 100011 that includes a cylindrical column frame stem 100012 and a cylindrical column frame pedestal 100013, with the stem 100012 depicted as having a button 100014 along the stem 100012. The stem 100012 is adapted to fit within, for example, a hinge cavity 90011 with the clamp 90010 in the open, unlocked position 90037, such that the pedestal 100013 and the hexagonal house 100011 are wider than the hinge cavity 90037 and prevent the tag 100010 from being removed from the clamp in the closed, locked position 90047 without tampering with the clamp 90010.

In some embodiments, the hexagonal housing 100011 take various other form factors including circular, spherical, domed, triangular, quadrilateral, and the like. The shape of the housing may vary as needed by the end user and/or required application but generally has no sharp edges, does not pose a hazard to third parties, is low weight, is compatible with umbilical cord clamps, has a waterproof (e.g., IP68) housing, is made of patient friendly, non-reactive materials, and can easily be cleaned without causing degradation to the housing. In order to help ensure the housing is waterproof, the housing may be sonically welded, have one or more rubber membranes, and/or a rubber or other water impermeable sleeve covering the housing.

Closure of the clamp 90010 closes the annular ring of the hinge cavity 90037 and depresses the button 100014, engaging a tamper-evident switch within the wireless tag 100010. In the event that the clamp 90010 is tampered with in a way that dislodges the stem 100012 from the hinge cavity 90037, the button 100014 may be dislodged from within the hinge cavity 90037 in a way that the button 100014 no longer is depressed or engaged, changing or interrupting the state of the tamper-evident switch to cause the system 10000 to interpret the interruption state change data as a possible tampering event that requires a response of an alert or an alarm, depending on the circumstances.

Figure 11A:
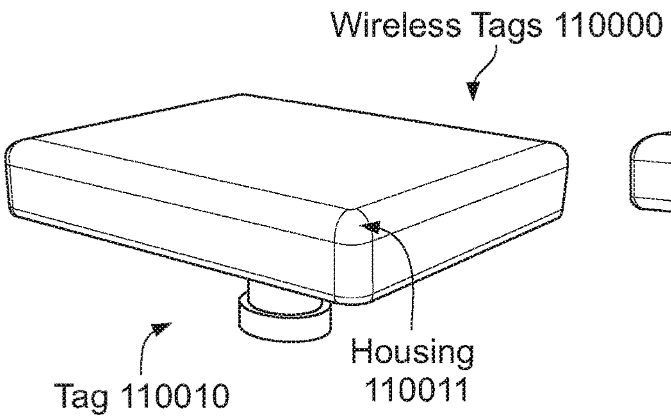
FIGS. 11A-11D shows depictions of other wireless tags from different viewpoints that may be used in an exemplary apparatus within a system used pursuant to a method in accordance with an exemplary embodiment of the present invention, according to aspects of the invention.
Figure 11B:
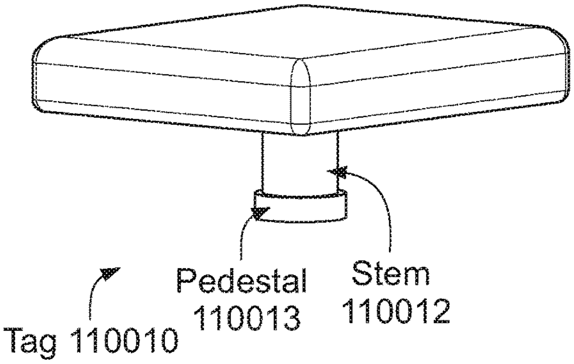
Figure 11C:
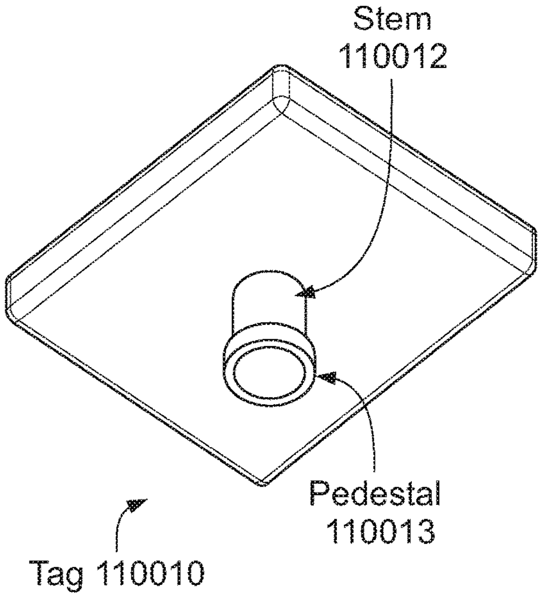
Figure 11D:
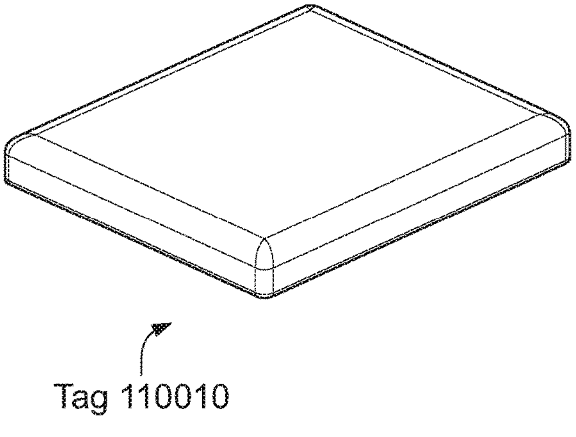

Referring to FIGS. 11A-11D, FIGS. 11A-11D shows depictions of other wireless tags 110000 and specific tag 110010 from different viewpoints that may be used in an exemplary apparatus within a system used pursuant to a method in accordance with an exemplary embodiment of the present invention, according to aspects of the invention. The embodiment of FIGS. 11A-11D shows an exemplary alternative embodiment of the system and is not limiting of the invention overall. FIG. 11A depicts a top perspective side view of tag 110010; FIG. 11B depicts another top perspective side view of tag 110010; FIG. 11C depicts a bottom perspective side view of tag 110010; and FIG. 11D depicts a top perspective plan view of tag 110010. Tag 110010 includes a rectangular housing 110011 that includes a cylindrical column frame stem 110012 and a cylindrical column frame pedestal 110013. Although not depicted, the stem 110012 may have along the stem 110012 a button analogous to button 100014. The stem 110012 is adapted to fit within, for example, a hinge and hinge cavity 90011 with the clamp 90010 in the open, unlocked position 90037, such that the pedestal 110013 and the rectangular house 110011 are wider than the hinge cavity 90037 and prevent the tag 110010 from being removed from the clamp in the closed, locked position 90047 without tampering with the clamp 90010. Closure of the clamp 90010 closes the annular ring of the hinge and hinge cavity 90037 and depresses the button, engaging a tamper-evident switch within the wireless tag 110010. In the event that the clamp 90010 is tampered with in a way that dislodges the stem 100012 from the hinge cavity 90037, the button may be dislodged from within the hinge cavity 90037 in a way that the button no longer is depressed or engaged, changing or interrupting the state of the tamper-evident switch to cause the system 10000 to interpret the interruption state change data as a possible tampering event that requires a response of an alert or an alarm, depending on the circumstances.

Figure 12A:
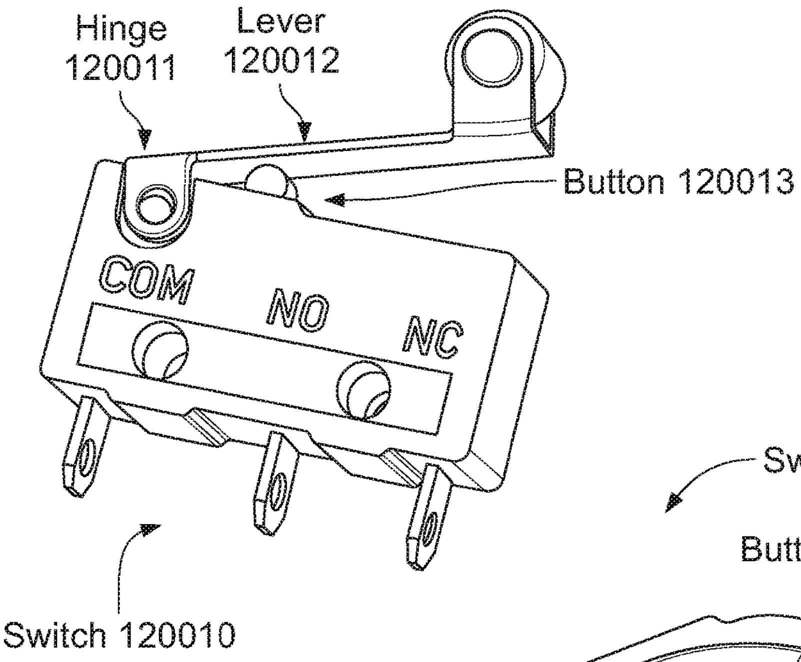
FIGS. 12A-12C shows depictions of switches from different viewpoints that may be used in an exemplary apparatus within a system used pursuant to a method in accordance with an exemplary embodiment of the present invention, according to aspects of the invention.
Figure 12B:
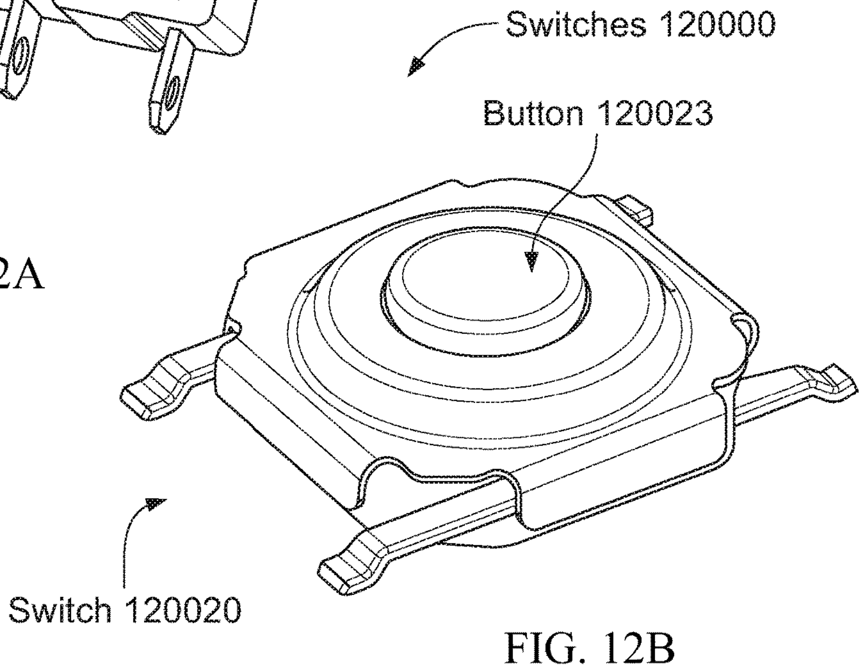
Figure 12C:
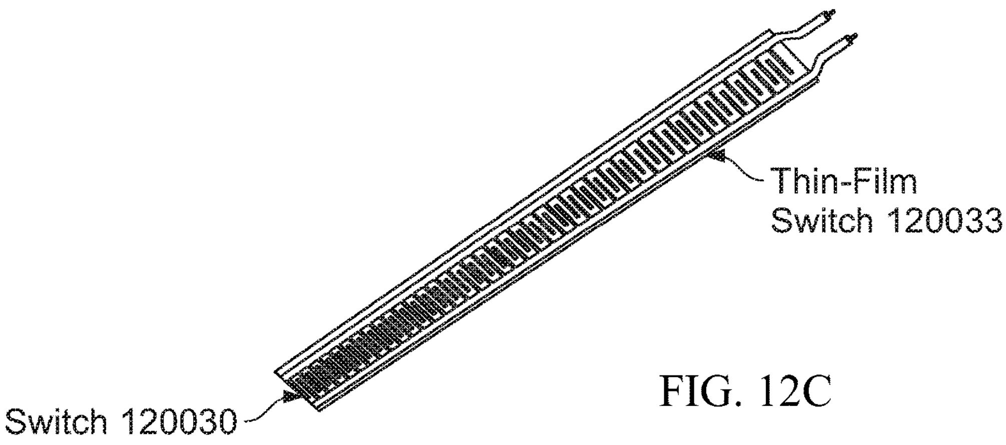

Referring to FIGS. 12A-12C, FIGS. 12A-12C show depictions of various switches 120000 and specific switches 120010, 120020, 120030 from different perspective viewpoints that may be used, alone or in combination, in an exemplary apparatus within a system used pursuant to a method in accordance with an exemplary embodiment of the present invention, according to aspects of the invention. The embodiments of FIGS. 12A-12C shows exemplary potential commercial embodiments of switches for use a wireless-enabled tag of a wireless-enabled clamp apparatus 11000 of the system 10000 and are not limiting of the invention overall. FIG. 12A depicts a switch 120010 having a hinge 120011, a hinged lever 120012, and a depressible button 120013, adapted to be engaged when the lever 120012 is pressed to close the hinge 120011, to activate the switch. FIG. 12B depicts a switch 120020 having an exposed depressible button 120023, adapted to be engaged when the button 120023 is pressed, to activate the switch. FIG. 12C depicts a switch 120030 having a compressible thin-film printed-circuit switch 120033, adapted to be engaged when the thin-film switch 120033 is compressed, to activate the switch.

These switches 120000, and variations thereof, may be adapted to serve a tamper-evident switch in a clamp apparatus 11000, such as in the ways described in reference to button 90039 in FIG. 9C and to button 100014 in FIG. 10D. For instance, button 90039 may comprise button 120023 of switch 120020 and be depressed by pin 90038. For instance, locking mechanism 90014 be fitted with switch 120010, in which lever 120012 acts as, or is engaged by, male portion 90015, to depress button 120013 upon closing the clamp 90010. For instance, button 100014 may comprise button 120023 of switch 120020 and be depressed by closure of hinge cavity 90011. For instance, thin-film switch 120033 may be positioned between and aligned with rows of teeth 90012, 90013, such that closing the clamp 90010 causes the rows of teeth 90012, 90013 to compress the thin-film switch 120033, such as when the umbilical cord is between the rows of teeth 90012, 90013, thereby engaging and activating the thin-film switch 120033. For instance, thin-film switch 120033 may be positioned around the stem 100012, 110012, such that closing the clamp 90010 causes the hinge cavity 90011 to compress the thin-film switch 120033, thereby engaging and activating the thin-film switch 120033. For instance, thin-film switch 120033 may be positioned around the male portion 90015, and/or within the female portion 90016, of locking mechanism 90014, such that closing the clamp 90010 causes the locking mechanism 90014 to compress the thin-film switch 120033, thereby engaging and activating the thin-film switch 120033.

The foregoing description discloses exemplary embodiments of the invention. While the invention herein disclosed has been described by means of specific embodiments and applications thereof, numerous modifications and variations could be made thereto by those skilled in the art without departing from the scope of the invention set forth in the claims. Modifications of the above disclosed apparatus and methods that fall within the scope of the claimed invention will be readily apparent to those of ordinary skill in the art. Accordingly, other embodiments may fall within the spirit and scope of the claimed invention, as defined by the claims that follow hereafter.

Figure 13A:
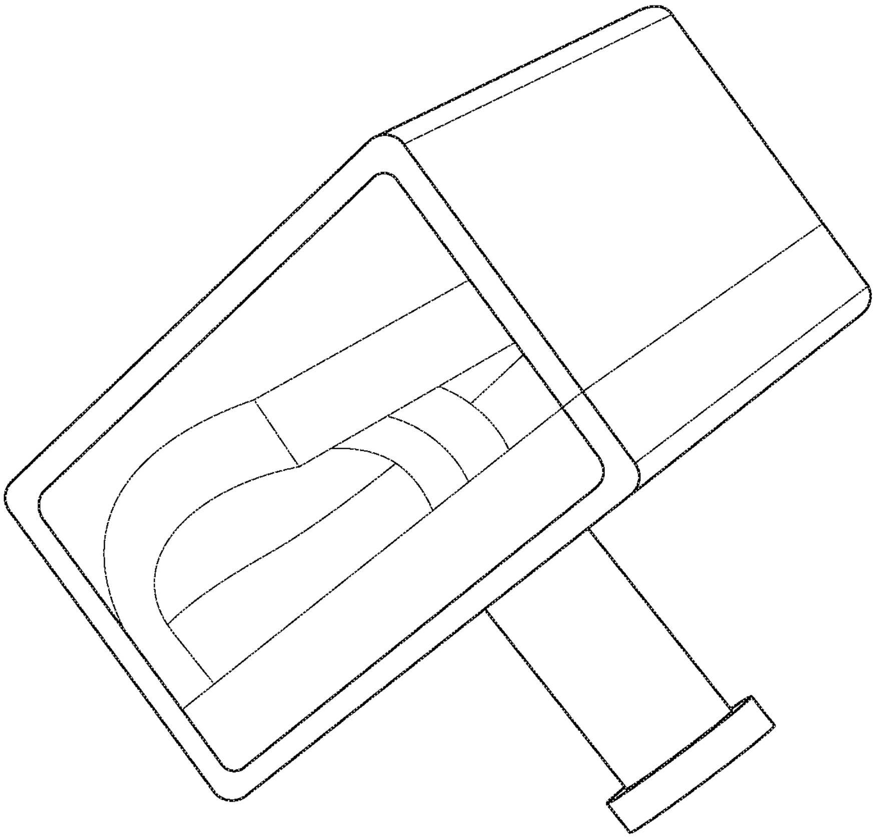
FIGS. 13A-C shows another embodiment of the wireless tag from different viewpoints that may be used as part of a system to monitor a status and/or location of the wireless tag.
Figure 13B:
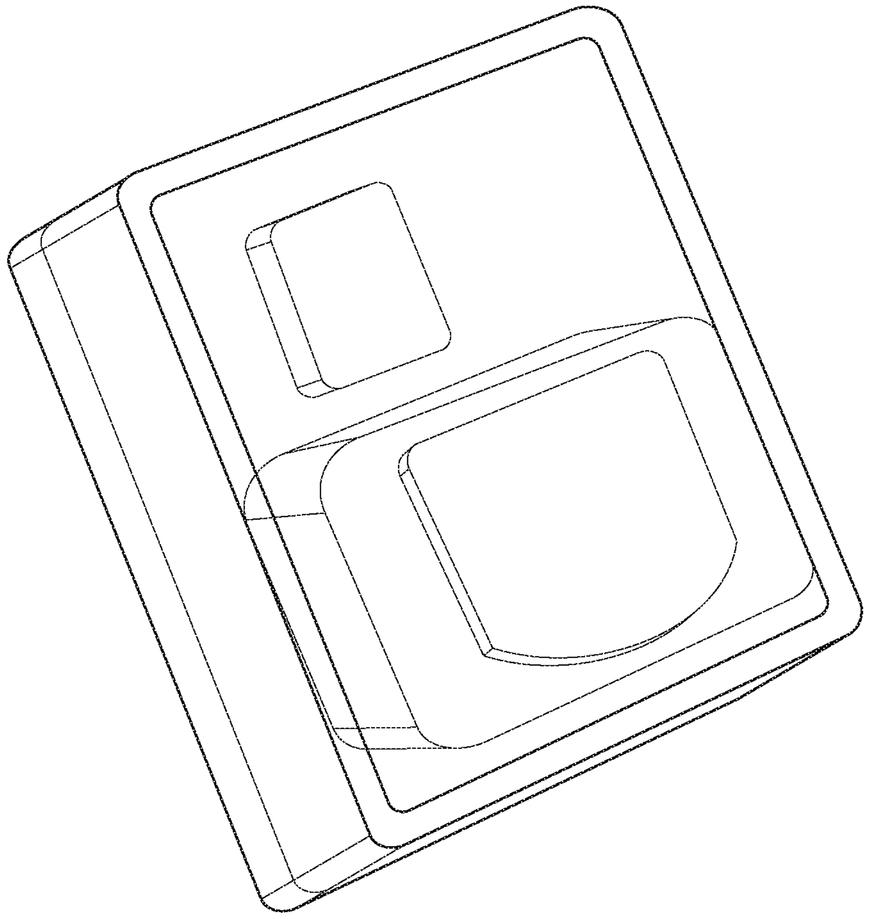
Figure 13C:
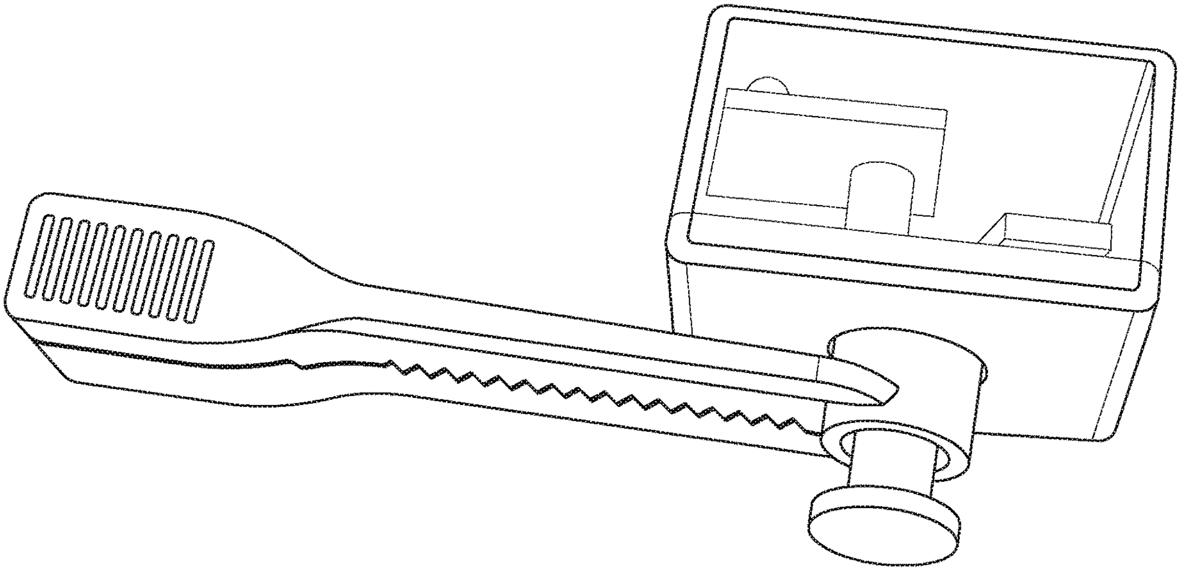

FIGS. 13A-C demonstrates another form factor of an embodiment of the present invention. The components and operation of the tag are consistent with the proceeding disclosure. Here, the exterior housing 11100 is a quadrilateral in shape and is clear. However, the exterior housing 11100 may be opaque. When the exterior housing 11100 is clear, it allows the internal components to be visible which may indicate operation or lack thereof (by a status LED) that would be visible to the user, service provider, etc.

In the description above, numerous specific details are set forth in order to provide a more thorough understanding of the embodiments of the invention. It will be apparent, however, to an artisan of ordinary skill that the invention may be practiced without incorporating all aspects of the specific details described herein. Not all possible embodiments of the invention are set forth verbatim herein. A multitude of combinations of aspects of the invention may be formed to create varying embodiments that fall within the scope of the claims hereafter. In addition, specific details well known to those of ordinary skill in the art have not been described in detail so as not to obscure the invention. Readers should note that although examples of the invention are set forth herein, the claims, and the full scope of any equivalents, are what define the metes and bounds of the invention protection.

What is claimed is:

1. A wireless-enabled tag for use with an umbilical cord clamp, the wireless-enabled tag comprising:
- a processor;
- a memory coupled to the processor;
- a wireless data transfer module coupled to the processor;
- a tamper-evident mechanism coupled to the processor,
  - wherein the tamper-evident mechanism comprises a switch coupled to the wireless-enabled tag,
  - wherein the switch is configured to be exposed to a hinge of the umbilical cord clamp when a locking mechanism of the umbilical cord clamp is in a secured position,
  - wherein the wireless-enabled tag is configured to be securely coupled to the umbilical cord clamp when the umbilical cord clamp is in a secured position, and
  - wherein the switch is configured to detect a first state and a second state,
    - wherein the first state is when the umbilical cord clamp is engaged with the switch, and
    - wherein the second state is when the umbilical cord clamp is disengaged from the switch.

2. The tag of claim 1, wherein the wireless-enabled tag further comprises a housing containing the processor, the memory, and the wireless data transfer module.

3. The tag of claim 1, wherein the wireless-enabled tag includes a rectangular housing containing the tag apparatus processor, the tag apparatus memory, the tag apparatus wireless data transfer module, and the tag apparatus wireless data transfer device.

4. The tag of claim 2, wherein the housing further comprises a column stem and a column pedestal.

5. The tag of claim 4, wherein the column stem is configured to fit in a hinge cavity of a hinge of the umbilical cord clamp.

6. The tag of claim 4, wherein the column pedestal is wider than the column stem and prevents the column stem from being removed from the hinge cavity when the umbilical cord clamp is in a locked position.

7. A wireless-enabled tag for use with an umbilical cord clamp, the wireless-enabled tag comprising:

a processor;

a memory coupled to the processor;

a wireless data transfer module coupled to the processor;

a power supply coupled to the processor;

a housing containing the processor, the memory, the wireless data transfer module, and the power supply, wherein the housing further comprises:

a column stem, a tag portion, and a column pedestal, wherein the column stem extends outwardly from the tag portion of the housing, wherein the column pedestal is located at a distal end of the column stem, wherein the column pedestal and the tag portion are both wider than the column stem, wherein the column stem is configured to be placed into a hinge of the umbilical cord clamp and secured in the hinge of the umbilical cord clamp when the umbilical cord clamp is in a secured position, and wherein the column pedestal and the tag portion prevent the column stem from being removed from the hinge when the umbilical cord clamp is in a secure position;

a tamper-evident mechanism coupled to the processor, wherein the tamper-evident mechanism comprises a switch configured to engage the hinge of the umbilical cord clamp, and wherein the switch is configured to be depressed when a male portion of the locking mechanism of the umbilical cord clamp engages a female portion of the locking mechanism of the umbilical cord clamp; and wherein the tag is adapted to be wirelessly read by a wireless tag reader.

* * * * *